United States Patent [19]

Kazuhiko et al.

[11] Patent Number: 4,973,425

[45] Date of Patent: * Nov. 27, 1990

[54] LIQUID CRYSTAL COMPOSITION AND USE THEREOF

[75] Inventors: Sakaguchi Kazuhiko, Toyonaka; Kasai Naoya, Amagasaki; Takehira Yoshikazu, Itami; Kitamura Tohru, Kyoto; Shiomi Yutaka, Amagasaki, all of Japan

[73] Assignee: Daiso Co., Ltd., Osaka, Japan

[*] Notice: The portion of the term of this patent subsequent to Mar. 20, 2007 has been disclaimed.

[21] Appl. No.: 398,264

[22] Filed: Aug. 24, 1989

[30] Foreign Application Priority Data

Aug. 25, 1988 [JP] Japan .................. 63-212093

[51] Int. Cl.$^5$ .............................. C09K 19/34
[52] U.S. Cl. ..................... 252/299.61; 350/350 S
[58] Field of Search ............... 252/299.61, 299.01; 350/350 S

[56] References Cited

U.S. PATENT DOCUMENTS

| | | | |
|---|---|---|---|
| 3,997,536 | 12/1976 | Boller et al. | 260/251 R |
| 4,066,570 | 1/1978 | Boller et al. | 252/299 |
| 4,596,667 | 6/1986 | Inukai et al. | 252/299.65 |
| 4,614,609 | 9/1986 | Inoue et al. | 252/299.66 |
| 4,780,241 | 10/1988 | Furukawa et al. | 252/299.63 |
| 4,818,431 | 4/1989 | Eidenschink et al. | 252/299.61 |
| 4,873,019 | 10/1989 | Krause et al. | 252/299.61 |
| 4,909,957 | 3/1990 | Sakaguchi et al. | 252/299.61 |

FOREIGN PATENT DOCUMENTS

| | | |
|---|---|---|
| 288813 | 11/1988 | European Pat. Off. |
| 313379 | 4/1989 | European Pat. Off. |
| 3739588 | 7/1988 | Fed. Rep. of Germany |

OTHER PUBLICATIONS

"Submicrosecond Bistable Electro-Optic Switching in Liquid Crystals", Clark et al., Appl. Phys. Lett. 36(11), Jun. 1, 1980, pp. 899–901.
"Ferroelectric Liquid Crystal Electro-Optics Using the Surface Stabilized Structure", Clark et al., Mol. Cryst. Liq. Cryst., 1983, vol. 94, pp. 213–233.
"Dipole Moments and the Smectic C Phase", Goodby et al., Mol. Cryst. Liq. Cryst., vol. 34 (Letters), 1977, pp. 183–188.

Primary Examiner—John S. Maples
Assistant Examiner—Richard Treanor
Attorney, Agent, or Firm—Wegner & Bretschneider

[57] ABSTRACT

Liquid crystal composition which comprises at least one liquid crystalline compound having an optically active γ-lactone ring of the formula (A):

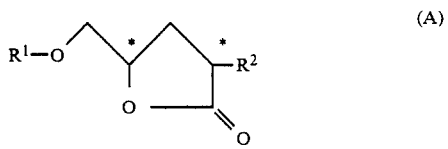

(A)

wherein $R^1$ is a group selected from the group consisting of

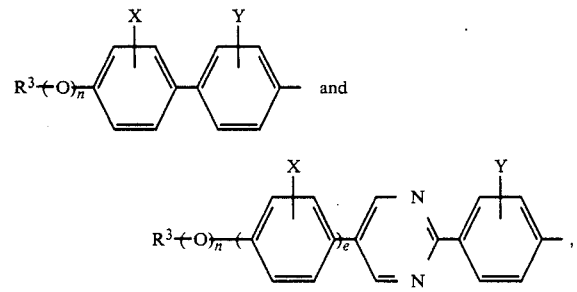

n and e are each independently 0 or 1; $R^3$ is an alkyl group having 1 to 15 carbon atoms; X and Y are each independently a group selected from the group consisting of hydrogen atom, a halogen atom and cyano group; $R^2$ is a group of the formula: $-(CO)_m-R^4$; m is 0 or 1; $R^4$ is hydrogen atom or an alkyl having 1 to 15 carbon atoms; and the symbol * is an asymmetric carbon atom, and a chiral or non-chiral liquid crystal, and a use thereof as an element for opto-electronics devices.

4 Claims, 4 Drawing Sheets

LIQUID CRYSTAL COMPOSITION AND USE THEREOF

This invention relates to a liquid crystal composition useful as an element for display devices or an element for opto-electronics devices.

PRIOR ART

Liquid crystals have widely been used as a material for display devices, where TN (Twisted Nematic) type display system is usually employed. This a TN display system has such advantages that it has less electric consumption, it gives less eye fatigue because it is a receptor type, and the like, but on the other hand, this system is disadvantageous in that the driving force is very weak because it is driven mainly on the basis of anisotropy of relative dielectric constant and it is slow in response speed, and hence, this system can not be applied to the devices which require high response speed.

A liquid crystal having ferroelectricity has first been found by R. B. Meyer et al. in 1975 (cf. J. Physique, 36, L-69, 1975). This liquid crystal is driven by a comparatively large force derived from spontaneous polarization and shows extremely high response speed and has also good memory. Owing to such excellent properties, the ferroelectric liquid crystal has been noticed as a new type of display element. In order to exhibit the ferroelectricity, the liquid crystalline compounds should show a chiral smectic C phase (SmC* phase) and thus should contain at least one asymmetric carbon atom in the molecule. It is also necessary to have a dipole moment in the direction vertical to the long axis of the molecule.

A ferroelectric liquid crystal DOBAMBC synthesized by Meyer et al. has the following formula:

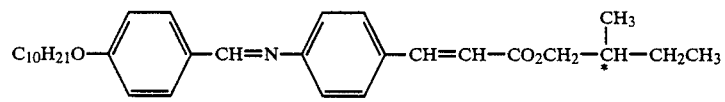

and satisfies the above conditions, but it contains a Schiff base and hence is chemically unstable and shows such a low spontaneous polarization as $3 \times 10^{-9}$ C/cm$^2$. Since then, there have been synthesized many ferroelectric liquid crystalline compounds, but any practically useful compound having sufficiently high response speed has never been found.

Among the known ferroelectric liquid crystalline compounds, DOBA-1-MBC which has the asymmetric carbon atom at the position nearer to the carbonyl group than in DOBAMBC and has the following formula:

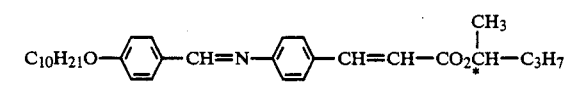

shows a spontaneous polarization of $5 \times 10^{-8}$ C/cm$^2$ which is larger than that of DOBAMBC. It is assumed that this will be caused by the following difference. That is, the asymmetric carbon atoms and the dipole which are important factors for the appearance of ferroelectricity are positioned close to each other, and thereby, the free rotation of the dipole moiety of the molecule is restricted and then the orientation of the dipole is increased. Thus, it is assumed that the known ferroelectric liquid crystalline compounds can not give satisfactory spontaneous polarization and high response speed because the asymmetric carbon atom having an inhibitory action on the free rotation of the molecule is present on the linear chain in the known ferroelectric liquid crystalline compounds and hence the free rotation of the molecule can not completely be inhibited and the dipole moiety can not be fixed.

SUMMARY OF THE INVENTION

Under the circumstances, the present inventors have intensively studied as to inhibition of free rotation of the dipole moiety in the conventional ferroelectric liquid crystalline compounds and have found that the free rotation can be inhibited by providing a compound wherein the asymmetric carbon atom is contained in a 5-membered lactone ring, by which there can be obtained a chemically stable liquid crystalline compound having ferroelectricity. The present inventors have already filed a patent application for said liquid crystalline compound. Thus, an object of the invention is to provide novel liquid crystal composition which comprises at least one of said liquid crystalline compounds, i.e. compounds having an optically active γ-lactone ring in the molecule wherein one or two asymmetric carbon atoms are present in the 5-membered lactone ring, or compounds having a specific substituent on the phenyl ring of the above compounds. Another object of the invention is to provide an element for opto-electronics devices comprising said liquid crystal composition. These and other objects and advantages of the invention will be apparent to those skilled in the art from the following description.

DETAILED DESCRIPTION OF THE INVENTION

Figure 1:
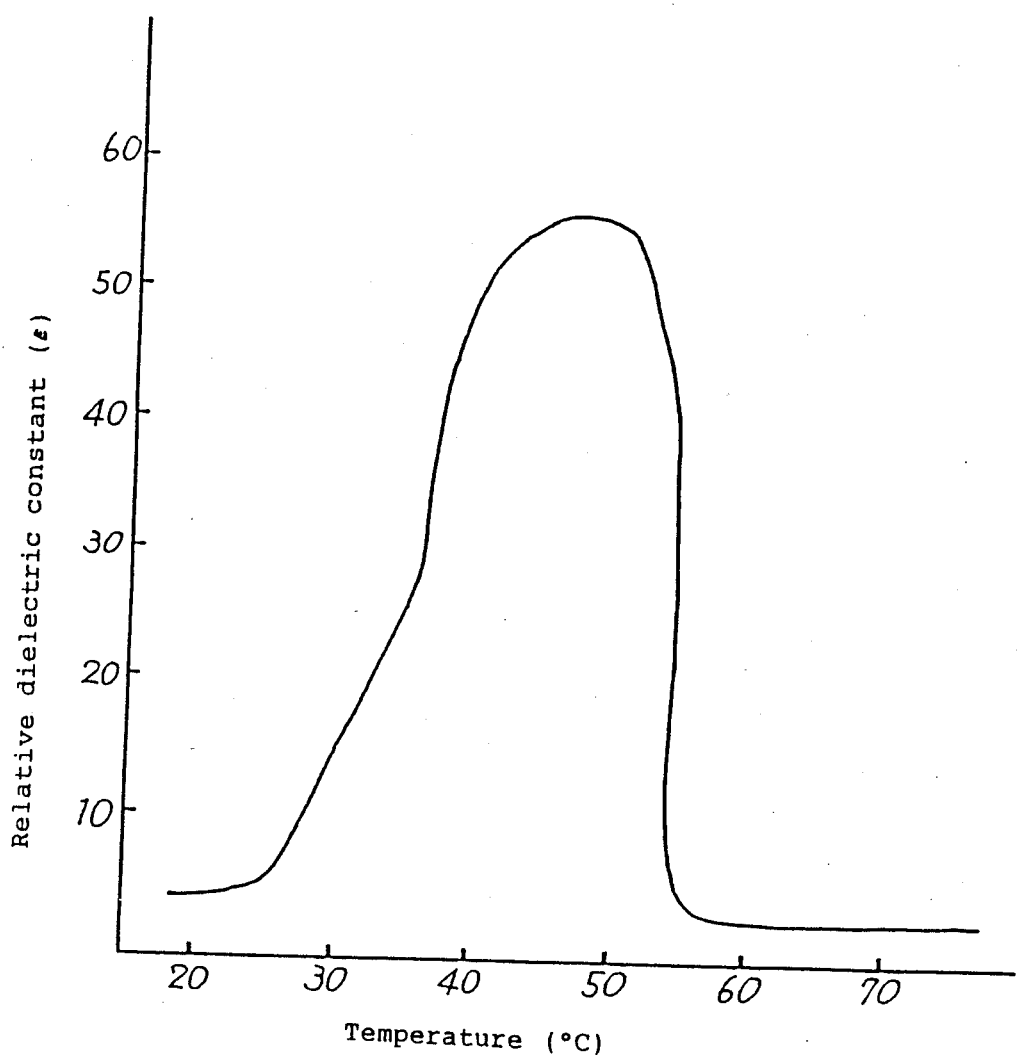
FIG. 1 shows a graph of the relation between the relative dielectric constant and temperature in the liquid crystal composition prepared in Example 1.

The liquid crystal composition of this invention comprises at least one liquid crystalline compound having optically active γ-lactone ring and having the following formula (A):

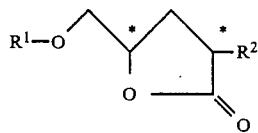

(A)

wherein $R^1$ is a group selected from the class group consisting of

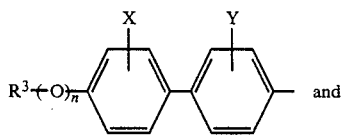

and

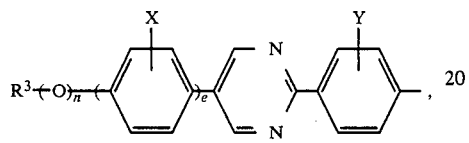

n and e are each independently 0 or 1; $R^3$ is an alkyl group having 1 to 15 carbon atoms; X and Y are each independently a group selected from the group consisting of hydrogen atom, a halogen atom and cyano group; $R^2$ is a group of the formula: $-(CO)_m-R^4$; m is 0 or 1; $R^4$ is hydrogen atom or an alkyl group having 1 to 15 carbon atoms; and the symbol * designates an asymmetric carbon atom, and a chiral or non-chiral liquid crystal.

In the specification, the term "alkyl group" for $R^3$ and $R^4$ includes methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, isopropyl, t-butyl, 2-methylpropyl, 1-methylpropyl, 3-methylbutyl, 2-methylbutyl, 1-methylbutyl, 4-methylpentyl, 3-methylpentyl, 2-methylpentyl, 1-methylpentyl, 5-methylhexyl, 4-methylhexyl, 3-methylhexyl, 2-methylhexyl, 1-methylhexyl, 6-methylheptyl, 5-methylheptyl, 4-methylheptyl, 3-methylheptyl, 2-methylheptyl, 1-methylheptyl, 7-methyloctyl, 6-methyloctyl, 5-methyloctyl, 4-methyloctyl, 3-methyloctyl, 2-methyloctyl, 1-methyloctyl, 8-methylnonyl, 7-methylnonyl, 6-methylnonyl, 5-methylnonyl, 4-methylnonyl, 3-methylnonyl, 2-methylnonyl, 1-methylnonyl, 3,7-dimethyloctyl, 3,7,11-trimethyldodecyl, and the like.

The compounds of this invention contain a carbonyl group within a 5-membered ring and one or two asymmetric carbon atoms on the ring as a moiety having a dipole moment as an origin of ferroelectricity, and hence, the free rotation at this moiety is inhibited and thereby the dipole moiety is directed to one direction, which is effective for enlarging the spontaneous polarization and for increasing the response speed. In the liquid crystalline compounds (A) of this invention, when the benzene ring(s) in $R^1$ has a substituent of a halogen atom or cyano group, the compound has a reduced melting point, a wider temperature range of chiral smectic C phase which is broadened to a low-temperature side and a larger tilt angle effective for increasing spontaneous polarization. Further, the introduction of a cyano group provides a compound having a large negative dielectric anisotropy, which negative dielectric anisotropy is necessary for driving the ferroelectric liquid crystal. When $R^2$ is a hydrogen atom, only one asymmetric carbon atom is contained, but when $R^2$ is a group other than hydrogen, two asymmetric carbon atoms are contained in the γ-lactone ring and hence there are present two kinds of diastereomer. These are all suitable for inhibition of free rotation of the dipole moiety, and they are used as a liquid crystal alone or in a mixture of two or more thereof. The liquid crystalline compound used in this invention includes not only the compound which is in the liquid crytalline state alone but also the compound which does not take the liquid crystalline form by itself but still is useful as a component of a liquid crystal composition.

The compounds (A) of the invention can be prepared by a process which comprises reacting an optically active glycidyl ether of the formula (B):

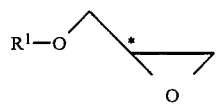

(B)

wherein $R^1$ and the symbol * are the same as $R^1$ and * in the formula (A), with a β-ketoester of the formula (C) or a malonate of the formula (D), respectively:

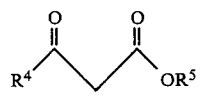

(C)

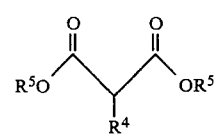

(D)

wherein $R^4$ is hydrogen atom or an alkyl group having 1 to 15 carbon atoms and $R^5$ is a lower alkyl group having 1 to 4 carbon atoms, in the presence of a base in an organic solvent.

The desired compound (A) of this invention can be prepared by reacting under reflux the compound (B) with 1 to 5 equivalents of the compound (C) or the compound (D) in the presence of 1 to 5 equivalents of a base in an organic solvent for 1.5 to 24 hours. The base used therein includes alkali metal alkoxides (e.g. sodium methoxide, sodium ethoxide, potassium t-butoxide, etc.), alkali metal hydrides (e.g. sodium hydride, lithium hydride, etc.), and alkyl alkali metals (e.g. n-butyllithium, etc.), and the organic solvent includes alcohols (e.g. methanol, ethanol, t-butyl alcohol, etc.), ethers (e.g. tetrahydrofuran, diethyl ether, dimethoxyethane, diethylene glycol dimethyl ether, dioxane, etc.), aprotic polar solvents (e.g. dimethylformamide, dimethylsulfoxide, hexamethylphosphoric triamide, etc.), and a mixture of these solvents.

In the above process, when $R^4$ in the compound (D) is a hydrogen atom, the final compound prepared by the above process is mixed with an inorganic salt (1 to 10 equivalents) and water under neutral condition and then is refluxed in a polar solvent to give the desired compound (A). The solvent used therein includes polar solvents such as dimethylformamide, dimethylacetamide, dimethylsulfoxide, hexamethylphosphoric triamide, diethylene glycol dimethyl ether, dioxane, and the like. The inorganic salt includes alkali metal or alkaline earth metal halides, such as lithium chloride, sodium chloride, potassium chloride, lithium bromide, sodium bromide, potassium bromide, lithium iodide, sodium iodide, potassium iodide, magnesium chloride, calcium chloride, strontium chloride, barium chloride, magnesium bromide, calcium bromide, barium bromide, magnesium iodide, calcium iodide, barium iodide, and the like. Water is preferably used in an amount of 5 to 50 equivalents. The reaction is completed in 1 to 15 hours.

The starting optically active glycidyl ether (B) can be prepared by a process as shown in the following reaction scheme:

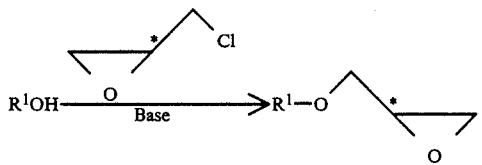

wherein $R^1$ and the symbol * are the same as $R^1$ and * in the formula (A).

That is, a phenol derivative of the formula $R^1OH$ is reacted with an optically active epichlorohydrin in the presence of a base. The optically active epichlorohydrin is preferably used in an amount of 1 to 10 equivalents to the phenol derivative, and the base is preferably used in an amount of 1 to 5 equivalents to the phenol derivative. The base includes alkali metal hydroxides or alkoxides, such as sodium hydroxide, potassium hydroxide, potassium t-butoxide, and the like. The above reaction may proceed smoothly without any catalyst, but may be carried out in the presence of a catalyst. The catalyst includes quaternary ammonium halides, such as benzyltriethylammonium chloride, benzyltriethylammonium bromide, benzyltrimethylammonium chloride, benzyltrimethylammonium bromide, etc. and is used in an amount of 0.01 to 0.1 equivalent to the phenol derivative. An excess amount of the optically active epichlorohydrin may be used as the solvent, but there is preferably used a suitable polar solvent such as dimethylformamide, dimethylsulfoxide, dimethylacetamide, acetonitrile, t-butyl alcohol, and water. The reaction is usually carried out at a temperature of 50° to 80° C. for 0.5 to 3 hours.

Alternatively, the optically active glycidyl ether (B) may also be prepared by reacting the phenol derivative of the formula $R^1OH$ with an optically active epichlorohydrin in the presence of an amine (e.g. morpholine, piperidine, pyridine, etc.) of 0.1 to 0.5 equivalent to the phenol derivative and subjecting the resulting optically active chlorohydrin derivative to a cyclization reaction with 1 to 5 equivalents of a base, such as an alkali metal hydroxide, carbonate or alkoxide (e.g. sodium hydroxide, potassium hydroxide, potassium carbonate, sodium carbonate, potassium t-butoxide, etc.). The latter process is carried out in two steps but is advantageous in that the extraction of the product can easily be done. This reaction is usually carried out at a temperature of 50° to 80° C. for 3 to 24 hours.

When a racemic epichlorohydrin is used in the above reaction, there is obtained a glycidyl ether in the form of a racemic mixture. The starting optically active epichlorohydrin can be prepared in a high purity by the processes as described in Japanese Patent First Publication (Kokai) Nos. 132196/1986 and 6697/1987 (as to R isomer) and by the process as described in Japanese Patent Application No. 283393/1987 (as to S isomer).

Besides, the starting phenol derivative used for the preparation of the compound (B) can be prepared by the processes as shown in the following Reaction Schemes-I to -VI, wherein $R^3$ is the same as $R^3$ in the formula (A), $R^{3'}$ is hydrogen atom or an alkyl group having a carbon atom one smaller than that in $R^3$, Ph means phenyl, and R' is a lower alkyl group having 1 to 4 carbon atoms.

That is, 4-(4-trans-alkylcyclohexyl)phenols, 4-(4-alkyloxyphenyl)phenols and 4-(4-alkylphenyl)phenols are prepared by the known processes as shown in Reaction Schemes-I, -II and -III, respectively.

REACTION SCHEME-I

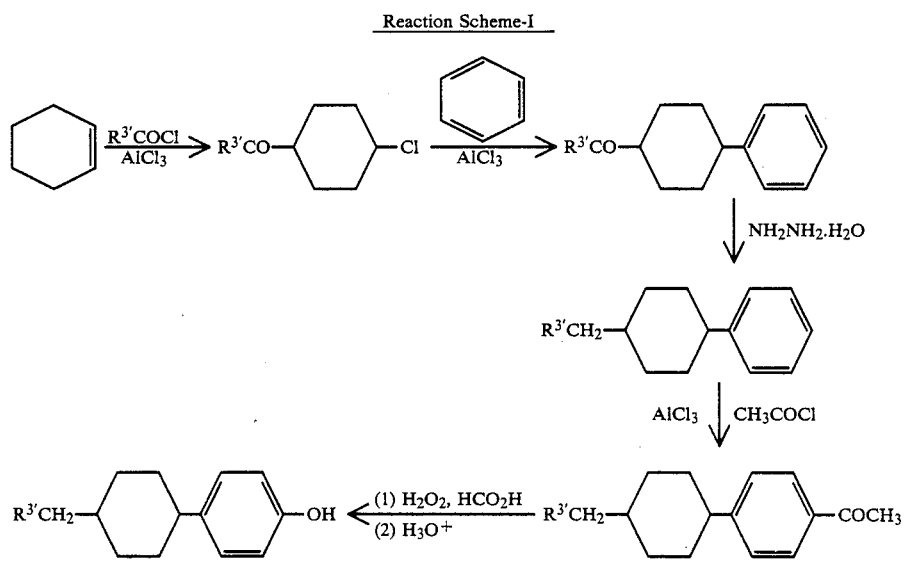

REACTION SCHEME-II
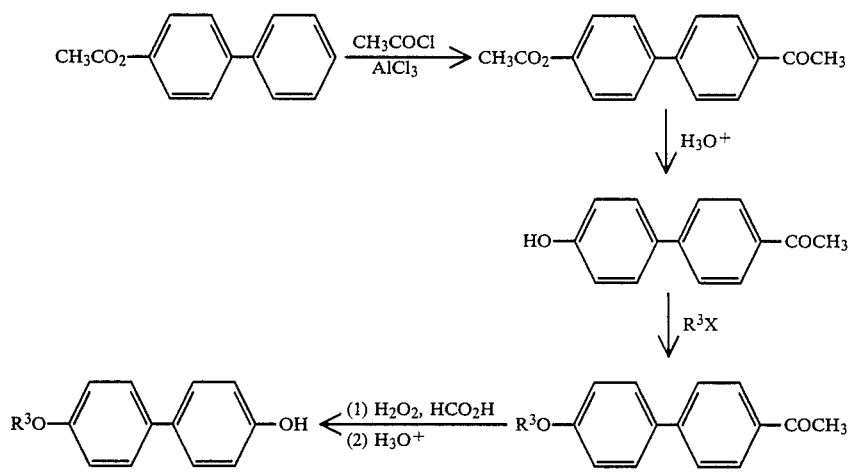
IV and -V, respectively, which are disclosed in Japanese Patent First Publication (Kokai) No. 189274/1986 and DE No. 144,409.
REACTION SCHEME-III
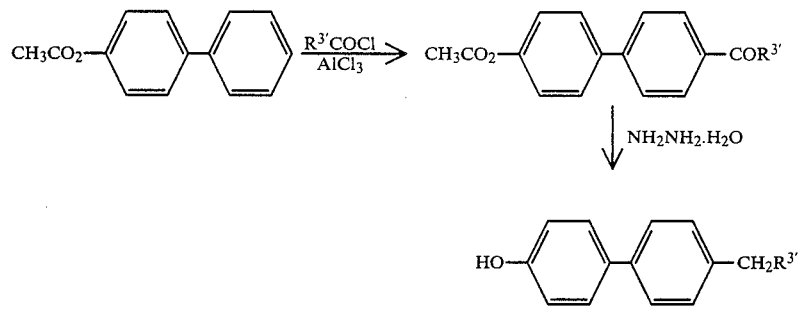
Besides, 4-(5-alkyl-2-pyrimidinyl)phenols and 4-(5-alkyloxy-2-pyrimidinyl)phenols are prepared by the processes as shown in the following Reaction Schemes-IV and -V, respectively.
REACTION SCHEME-IV
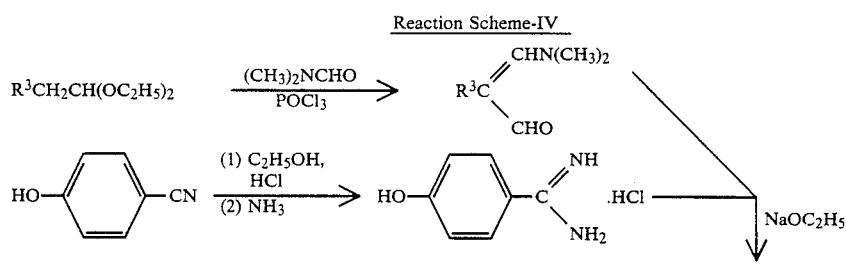

-continued
Reaction Scheme-IV
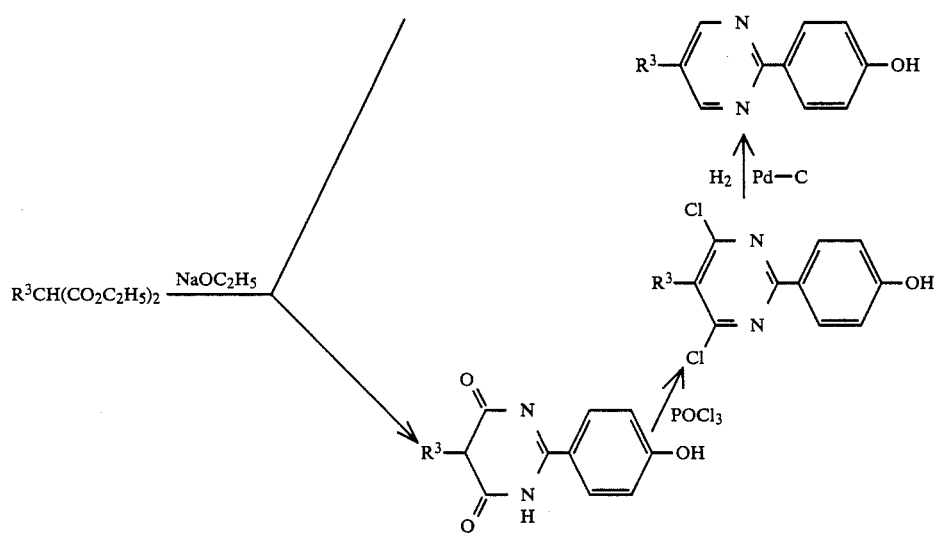
REACTION SCHEME-V
are prepared by the processes as shown in the following Reaction Scheme-VI.
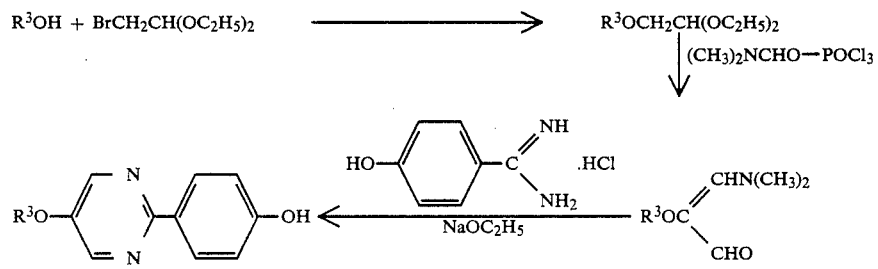
Moreover, 4-[5-(4-alkyloxyphenyl)-2-pyrimidinyl]-phenols and 4-[5-(4-alkylphenyl)-2-pyrimidinyl]phenols
REACTION SCHEME-VI
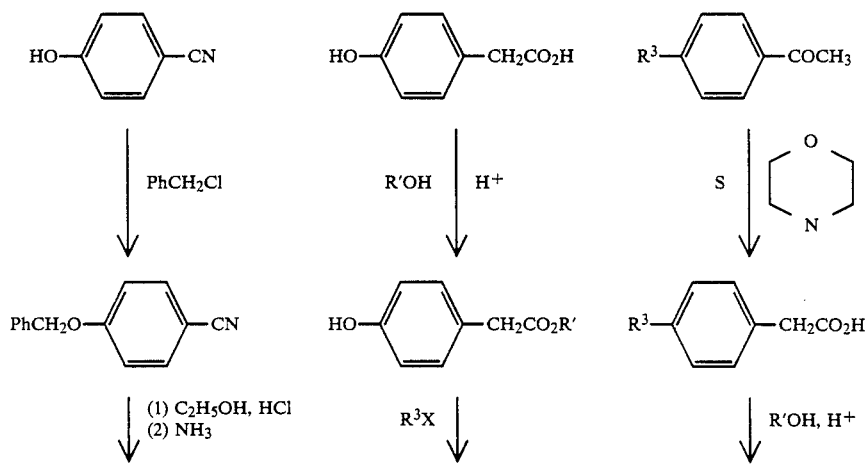

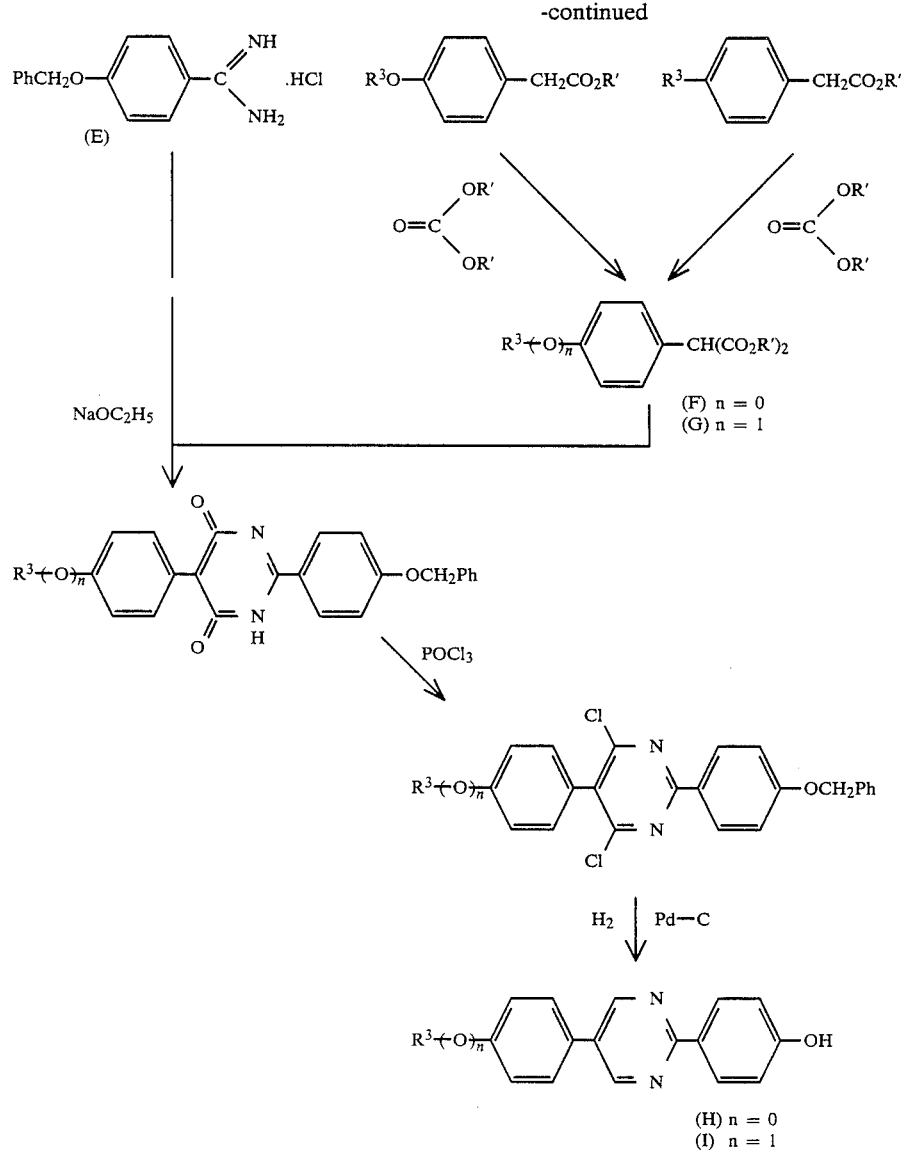

According to the process of Reaction Scheme-VI, Compound (E) is prepared by protecting the hydroxy group of p-hydroxybenzonitrile with a benzyl group and converting the cyano group thereof into amidine hydrochloride in a usual manner. Separately, p-hydroxyphenylacetic acid is esterified with a lower alcohol, and the phenolic hydroxy group is alkylated with an alkylating agent such as an alkyl halide, an alkyl p-toluenesulfonate or an alkyl methanesulfonate, followed by reacting with diethyl carbonate in the presence of a base to give diethyl malonate derivative (G).

The amidine hydrochloride (E) is condensed with the diethyl malonate derivative (G) in the presence of a base such as alkali metal alkoxides (e.g. sodium ethoxide, sodium methoxide, etc.), followed by reacting with phosphorus oxychloride in the presence of a base such as organic amines (e.g. N,N-diethylaniline, pyridine, 4-(N,N-dimethylamino)-pyridine, etc.), and the resulting compound is reduced with hydrogen gas in the presence of Pd-C catalyst to give the desired 4-[5-(4-alkyloxyphenyl)-2-pyrimidinyl]phenol (I).

In the above process, when a diethyl p-alkylphenylmalonate (F) is used instead of the diethyl malonate derivative (G) and the compound (E) and the compound (F) are reacted like in the reaction of the compound (E) and the compound (G), there is prepared 4-[5-(4-alkylphenyl)-2-pyrimidinyl]phenol (H).

The diethyl p-alkylphenylmalonate (F) can be prepared by subjecting a p-alkylacetophenone to a Willgerodt reaction, esterifying the resulting phenylacetic acid derivative with a lower alcohol, and condensing the resultant with diethyl carbonate.

Moreover, among the starting phenol derivatives used for the preparation of the compound (B), the phenol derivative wherein the benzene ring is substituted with a halogen atom or cyano group, can be prepared by the processes as shown in the following Reaction Schemes-VII to -XI, wherein $R^3$, $R^{3'}$ and X are the same as defined in the above Reaction Schemes-I to VI and Ts means p-toluene-sulfonyl group. That is, 4-(4-alkylphenyl)-2-halogenophenols and 4-(4-alkylphenyl)-2-cyanophenols are prepared by the process as shown in Reaction Scheme-VII.

Reaction Scheme-VII

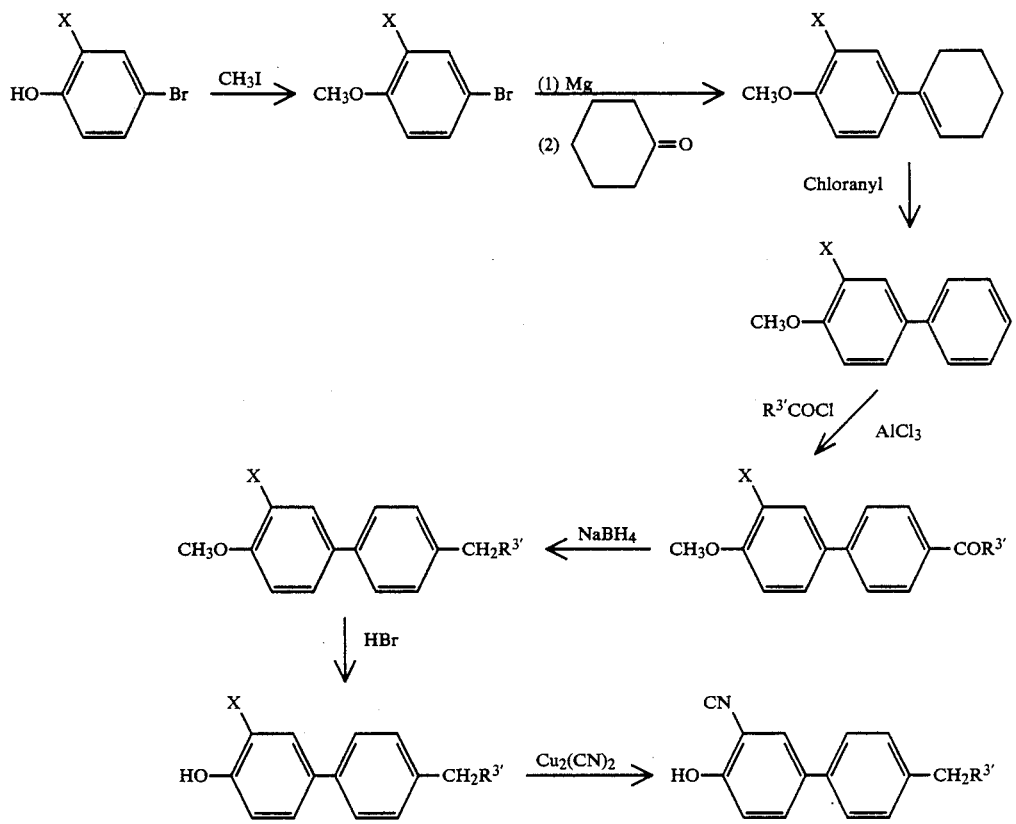

Besides, 4-(4-alkoxyphenyl)-2-halogenophenols and 4-(4-alkoxyphenyl)-2-cyanophenols are prepared by the known process as shown in the following Reaction Scheme-VIII, which is disclosed Japanese Patent First Publication (Kokai) No. 166646/1985.

REACTION SCHEME-VIII

Moreover, 4-(4-alkoxy-3-florophenyl)phenols are prepared by the known process as shown in the following Reaction Scheme-IX, which is disclosed in Abstract of the 12th Liquid Crystal Symposium, Nagoya, Japan, No. 2, F18, 1986.

REACTION SCHEME-IX

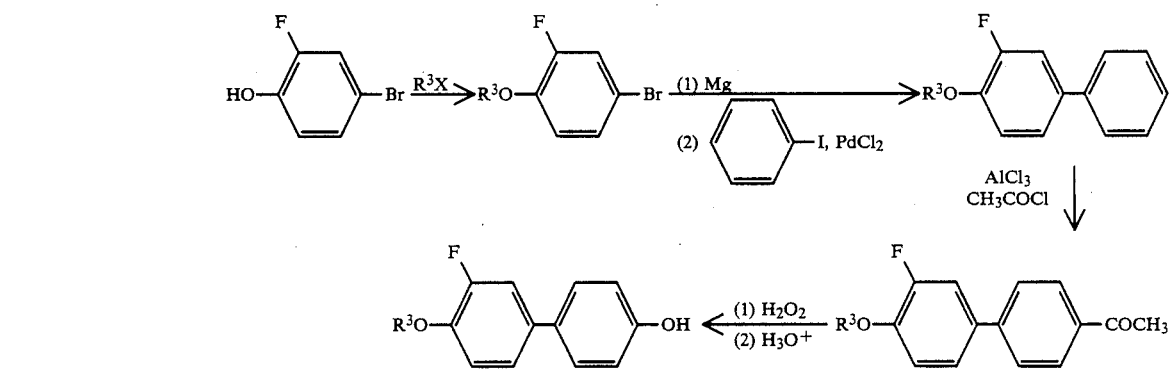

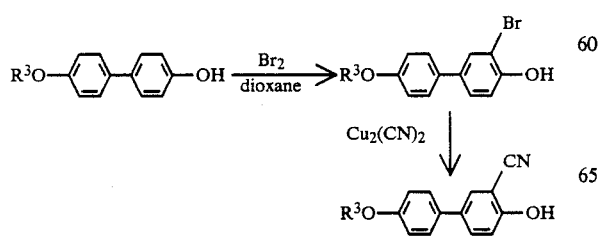

Besides, 4-(4-alkoxy-3-bromophenyl)phenols and 4-(4-alkoxy-3-cyanophenyl)phenols are prepared by the known process as shown in the following Reaction Scheme-X, which is disclosed in Japanese Patent First Publication (Kokai) No. 66646/1985.

REACTION SCHEME-X

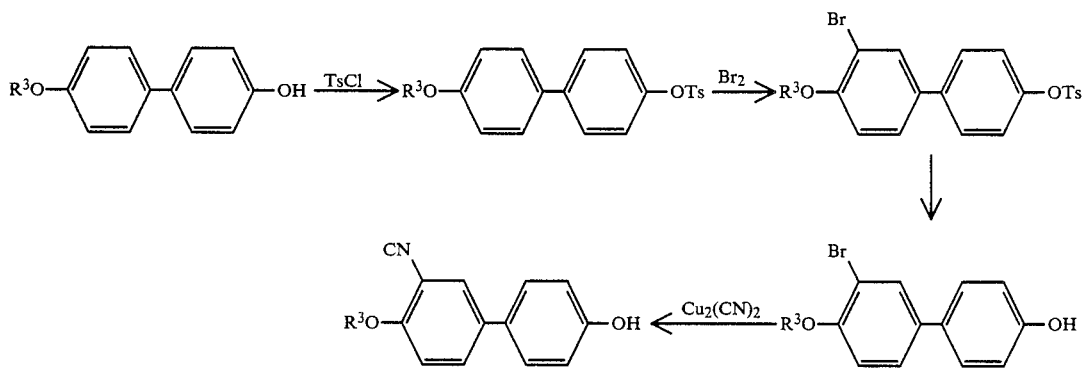

Moreover, 4-(4-alkyl-2-pyrimidinyl)-2-halogenophenols and 4-(5-alkyl-2-pyrimidinyl)-2-cyanophenols are prepared by the known process as shown in the following Reaction Scheme -XI, which is disclosed in Abstract of the 13th Liquid Crystal Symposium, Fukuoka, Japan, 1Z 06, 1987.

REACTION SCHEME-XI

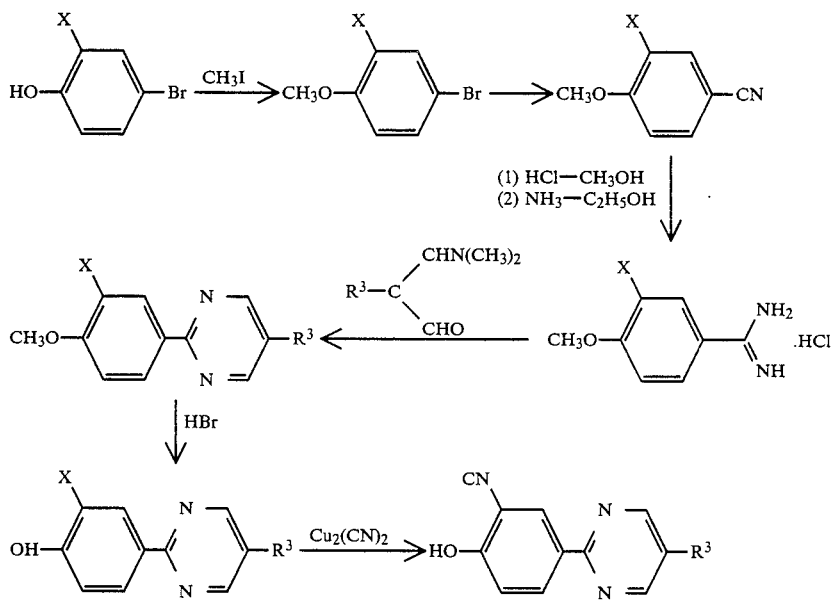

Besides, 4-(4-alkylphenyl)-2-cyanophenols are prepared by the known process as shown in the following Reaction Scheme-XII, which is disclosed in Japanese Patent First Publication (Kokai) No. 165331/1988.

Reaction Scheme-XII

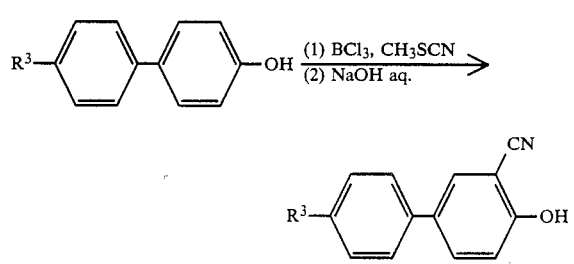

The liquid crystal composition of this invention may be obtained by mixing at least one of the compound (A) as prepared above with a chiral or non-chiral liquid crystal.

The chiral or non-chiral liquid crystal employed in the liquid crystal composition of this invention is not particularly limited but may be any conventional chiral or non-chiral liquid crystal which shows chiral smectic C phase after mixing with the compound (A).

Typical example of the above chiral or non-chiral liquid crystal includes the compound of the general formula (J):

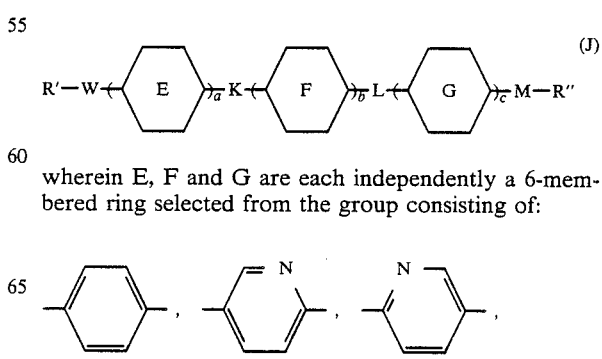

wherein E, F and G are each independently a 6-membered ring selected from the group consisting of:

-continued

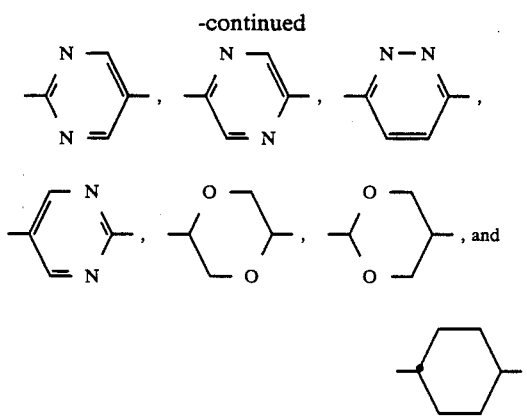

the hydrogen atom(s) in the 6-membered ring being optionally substituted with a halogen atom, cyano group or nitro group; a and b are each 0, 1 or 2 and c is 1 or 2, but $a+b+c=2$ to 4; W and M are each a single bond or a group selected from the group consisting of

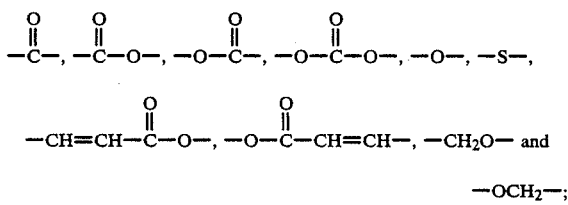

K and L are each independently a single bond or a group selected from the class consisting of

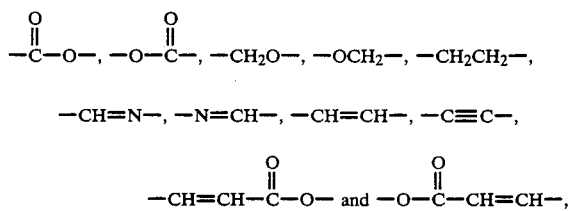

provided that K is a single bond when $a=0$, and L is a single bond when $b=0$; R' and R'' are each independently an alkyl group having 1 to 15 carbon atoms, which may contain one or more asymmetric carbon atoms.

Particularly suitable examples of the chiral or non-chiral liquid crystal are a compound of the formula (J-1):

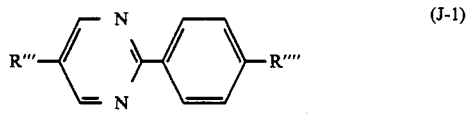

wherein R''' and R'''' are the same or different and are each a straight chain or branched chain alkyl group having 1 to 15 carbon atoms or a straight chain or branched chain alkoxy group having 1 to 15 carbon atoms, said alkyl and alkoxy groups having optionally one or more asymmetric carbon atoms, and a compound of the formula (J-2):

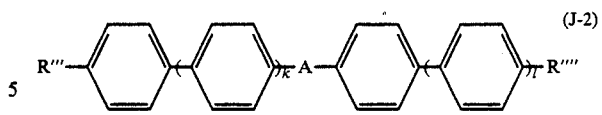

wherein R''' and R'''' are as defined above, A is

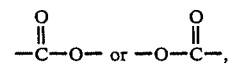

and k and l are independently 0 or 1, but $k+l\neq 2$.

The liquid crystal composition of this invention is useful for preparing a liquid crystal cell of an electrically controlled birefrigence mode or guest-host mode, which is prepared by attaching a transparent electrode to the liquid crystal composition of this invention, sandwiching the resultant electrode-attached liquid crystal composition with two sheets of glass plate which is surface-treated for orientation with a polymer (e.g. polyethylene, polyester, nylon, polyvinyl alcohol, polyimide, etc.), and providing a polarizer. The thus prepared liquid crystal cell can be used as an element for display devices or an element for opto-electronics devices.

The liquid crystalline compounds (A) of this invention may be obtained in the form of a racemic mixture when a racemic epichlorohydrin is used as the starting material, and the racemic compounds may be added to other optically active liquid crystalline compounds in order to regulate the helical pitch thereof. The liquid crystalline compounds (A) of this invention have excellent heat stability and light stability, and the liquid crystal composition comprising the liquid crystalline compound (A) shows excellent properties as ferroelectric liquid crystal. The Liquid crystal composition comprising the liquid crystalline compound (A) of this invention and nematic liquid crystal is (1) Liquid crystal composition of TN (Twisted also useful for the following utilities. Nematic) type or STN (Super Twisted Nematic) type liquid crystals wherein the compound (A) is effective to inhibit occurrence of reverse domain.

(2) Display element utilizing cholesteric-nematic phase transfer effects (cf. J. J. Wysoki, A. Adams and W. Haas; Phys. Rev. Lett., 20, 1024, 1968).

(3) Display element utilizing White-Taylor type guest-host effects (cf. D. L. White and G. N. Taylor; J. Appl. Phys., 45, 4718, 1974).

(4) Notch filter or band-pass filter utilizing selective scattering effects by fixing the cholesteric phase in matrix (cf. F. J. Kahn; Appl. Phys. Lett., 18, 231, 1971).

(5) Circularly polarized light beam splitter utilizing circularly polarized light characteristics of the cholesteric phase (cf. S. D. Jacob; SPIE. 37, 98, 1981).

As mentioned above, the liquid crystal composition of this invention comprises the optically active γ-lactone liquid crystalline compound, and due to a large spontaneous polarization and chemical stability of said compound, shows a more rapid response speed and higher chemical stability than those of the conventional liquid crystal composition.

This invention is illustrated by the following Preparations, Examples and Comparative Example, but should not be construed to be limited thereto.

In Examples, the positions of R and S in the optically active compounds (A) of this invention are shown by the position numbers in the following formula:

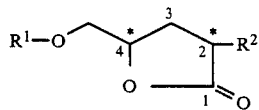

The phase transfer temperature in Examples was measured by DSC (Differential Scanning Colorimetry) and a polarizing microscope. Besides, the symbols in the phase transfer temperature have the following meaning:
C: Crystalline phase
SmA: Smectic A phase
SmC: Smectic C phase
SmC*: Chiral smectic C phase
SmI: Non-identified smectic phase other than SmA, SmC and SmC*.
N: Nematic phase
N*: Chiral nematic phase
I: Isotropic liquid The chiral smectic C phase (SmC*) was further confirmed by measuring relative dielectric constant thereof.

PREPARATION OF PHENOL DERIVATIVES

Preparation 1

Preparation of 4-[5-(4-n-octyloxyphenyl)-2-pyrimidinyl]phenol:

(i) Preparation of 4-benzyloxyphenylamidine hydrochloride:

4-Cyanophenol (95.2 g), benzyl chloride (127 g) and potassium carbonate (138 g) are refluxed in acetone (160 ml) for 5 hours. The product is separated by filtration, concentrated under reduced pressure, and thereto is added benzene. The mixture is washed with water, and benzene is distilled off under reduced pressure to give 4-benzyloxybenzonitrile (141.38 g). The 4-benzyloxybenzonitrile (141 g) is dissolved in benzene (338 ml) and thereto is added ethanol (270 ml), and the mixture is cooled to 0° C. Into the resulting slurry is bubbled hydrogen chloride gas (36 liters) with stirring, and thereafter, the temperature is raised to 25° C., and the mixture is allowed to stand for 2 days. The reaction mixture is concentrated under reduced pressure until ⅓ volume, and to the concentrated mixture is added ether. The precipitated crystals are separated by suction filtration to give an imide ester (183 g).

The above-obtained imide ester (183 g) is mixed with ethanol (270 ml) to give a slurry, and thereto is added a solution of ammonia (60.75 g) in ethanol (405 ml). After allowing the mixture to stand at room temperature for 2 days, the solvent is distilled off under reduced pressure to give 4-benzyloxyphenylamidine hydrochloride (164.5 g).

NMR (DMSO-$d_6$) δ: 5.19 (2H, s), 7.17 (2H, d, J=9.0 Hz), 7.35 (5H, s), 7.86 (2H, d)

(ii) Preparation of diethyl 4-n-octyloxyphenylmalonate:

4-Hydroxyphenylacetic acid (50.0 g) is dissolved in ethanol (400 ml) and thereto is added conc. sulfuric acid (0.5 ml). The mixture is refluxed with stirring, and ethanol is distilled off to give ethyl 4-hydroxyphenylacetate (60 g).

The ethyl 4-hydroxyphenylacetate (59 g) and sodium ethoxide (22.4 g) are dissolved in ethanol (150 ml) and thereto is added n-octyl bromide (63.5 g), and the mixture is refluxed for 3 hours and concentrated under reduced pressure, and thereto is added ethyl acetate to dissolve the oily substance. The mixture is washed with water, dried over anhydrous magnesium sulfate, distilled under reduced pressure to remove ethyl acetate, and further distilled under reduced pressure to give ethyl 4-n-octyloxyphenylacetate (79.6 g, b.p. 179° C./0.1 mmHg).

The obtained ethyl 4-n-octyloxyphenylacetate (79 g), ethanol (140 ml), diethyl carbonate (300 ml) and sodium ethoxide (19.3 g) are mixed, and the mixture is heated with stirring while ethanol is distilling off. The reaction mixture is transferred into ice water and is acidified with hydrochloric acid. The organic layer is separated and the solvent is distilled off to give diethyl 4-n-octyloxyphenylmalonate (91.6 g).

NMR (CDCl$_3$) δ: 0.5–2.0 (21H, m), 3.90 (2H, t, J=6.0 Hz), 4.16 (4H, q, J=7.2 Hz), 4.52 (1H, s), 6.80 (2H, d, J=9.0 Hz), 7.26 (2H, d, J=9.0 Hz)

(iii) Preparation of 4-[5-(4-n-octyloxyphenyl)-2pyrimidinyl]phenol:

4-Benzyloxyphenylamidine hydrochloride (65.6 g) and diethyl 4-n-octyloxyphenylmalonate (91.0 g) are dissolved in methanol (500 ml) and thereto is added sodium methoxide (44.8 g), and the mixture is refluxed with stirring for 9 hours. After cooling, the reaction mixture is acidified with sulfuric acid, and the precipitated crystals are separated by suction filtration to give yellow crystals (77.7 g).

The above yellow crystals (77 g), phosphorus oxychloride (310 ml) and N,N-diethylaniline (46.5 ml) are mixed and refluxed with stirring for 26 hours. The excess phosphorus oxychloride is distilled off under reduced pressure, and the residue is transferred into icewater and extracted with ether. The extract is washed with water and distilled to remove ether to give a crude product (70 g). The product is recrystallized from ether to give a compound (21 g) of the following formula:

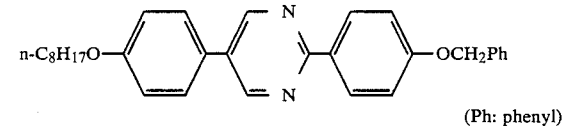

(Ph: phenyl)

NMR (CDCl$_3$) δ: 0.4–2.1 (15H, m), 3.99 (2H, t, J=6.0 Hz), 5.09 (2H, s), 6.7–7.5 (11H, m), 8.38 (2H, d, J=9.0 Hz)

The colorless crystals obtained above (19.8 g), ethanol (757 ml), magnesium oxide (11.4 g), water (57 ml) and 10% Pd-C (4 g) are heated with stirring at 60° C. under hydrogen atmosphere until a theoretical amount of hydrogen is absorbed. The reaction mixture is filtered with suction, and the filtrate is concentrated to give the desired 4-[5(4-n-octyloxyphenyl)-2-pyrimidinyl]phenol (7.7 g) of the following formula:

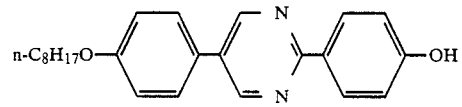

m.p. 137° C.

NMR (CDCl$_3$) δ: 0.5–2.1 (15H, m), 4.00 (2H, t, J=6.0 Hz), 6.92 (2H, d, J=9.0 Hz), 7.01 (2H, d, J=9.0 Hz), 7.50 (2H, d, J=9.0 Hz), 8.30 (2H, d, J=9.0 Hz), 8.94 (2H, s)

PREPARATION OF THE COMPOUNDS (B):

The starting optically active epichlorohydrins are prepared by the processes as disclosed in Japanese Patent First Publication (Kokai) Nos. 132196/1986 and 6697/1987 and in Japanese Patent Application No. 283393/1987. These are R—(—)— and S—(+)—epichlorohydrins which have a chemical purity of 98.5% or more (measured by gas chromatographic analysis) and an optical purity of 99% or more [the specific rotation, $[\alpha]_D{}^{25}= -34.0°$, c=1.2, methanol, respectively].

Preparation 2

To a suspension of 4-(4-n-octylphenyl)phenol (2.82 g) in 1,2-dichloroethane (40 ml) is added a 2M borone trichloride - 1,2-dichloroethane solution (6 ml) under ice cooling, and thereto are further added methyl thiocyanate (0.82 ml) and aluminum chloride (1.33 g). The mixture is stirred at room temperature until aluminum chloride is dissolved, and is further stirred at 80° C. for 3 hours. After cooling, 4N aqueous sodium hydroxide solution (33 ml) is added to the reaction mixture, and the mixture is stirred at 75°–80° C. for 30 minutes. After cooling, the reaction mixture is washed with methylene chloride, and the aqueous layer is adjusted to pH 2 with 6N hydrochloric acid and then extracted with ether. The extract is dried and then ether is distilled off under reduced pressure. The crude crystal thus obtained is purified by silica gel column chromatography to give 4-(4-n-octylphenyl)-2-cyanophenol (2.03 g) of the following formula:

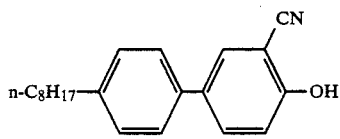

m.p. 93° C.
$^1$H-NMR (CDCl$_3$) δ: 0.88 (3H, t, J=6.8 Hz), 1.27–1.32 (10H, m), 1.60–1.71 (2H, m), 2.64 (2H, t, J=7.7 Hz), 6.24 (1H, broad s), 7.02–7.70 (7H, m)
IR (KBr): 3288 cm$^{-1}$($\gamma_{O-H}$), 2240 cm$^{-1}$($\gamma$C≡N)

Preparation 3

The above R—(—)—epichlorohydrin (4.25 g), the starting phenol derivative (2.50 g) of the following formula:

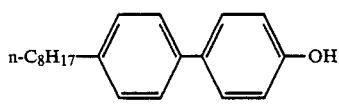

and benzyltriethylammonium chloride (20 mg) are dissolved in dimethylformamide (3 ml) and thereto is added dropwise 24 wt. % aqueous sodium hydroxide (1.2 equivalent) at 60° C. After reacting at the same temperature for 40 minutes, the reaction mixture is cooled to room temperature and extracted with ether. The extract is distilled under reduced pressure to remove the solvent. The residue is purified by silica gel chromatography to give S isomer of a glycidyl ether (1.62 g) of the following formula:

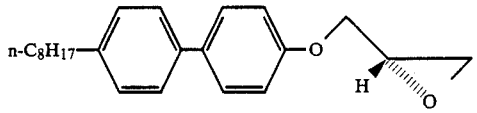

m.p. 90° C.
$[\alpha]_D{}^{25}= +4.44°$(c=1.0., CH$_2$Cl$_2$)
NMR (CDCl$_3$) δ: 0.50–3.00 (19H, m), 3.10–3.50 (1H, m), 3.80–4.30 (2H, m), 6.75–7.60 (8H, m)

Preparation 4

The starting phenol derivative (13 g) of the following formula:

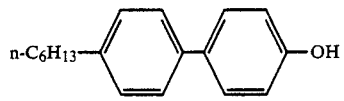

and the same R—(—)—epichlorohydrin (13.2 g) as used in Preparation 3, potassium t-butoxide (8.8 g) and t-butyl alcohol (80 ml) are mixed and stirred at 60° C. for 2 hours. After the reaction mixture is concentrated, chloroform is added to the concentrate and the resultant is washed with a saturated saline solution and dried over anhydrous magnesium sulfate. Chloroform is distilled away under reduced pressure to give a crude product. The crude product is purified by silica gel column chromatography to give S isomer of a glycidyl ether (14.2 g) of the following formula:

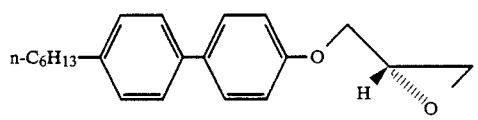

m.p. 90° C.
$[\alpha]_D{}^{30}= +4.78°$ (c=1.082, CH$_2$Cl$_2$)
NMR (CDCl$_3$) δ: 0.88–3.0 (15H, m), 3.10–3.50 (1H, m), 3.80–4.40 (2H, m), 6.85–7.60 (8H, m)

Preparation 5

The procedures of Preparation 4 are repeated except that the starting phenol derivative of the following formula:

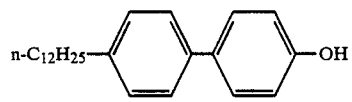

is employed and the above S—(+)—epichlorohydrin is employed in place of R—(—)—epichlorohydrin to give R isomer of a glycidyl ether of the following formula:

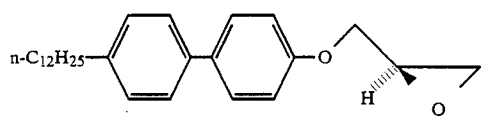

m.p. 91° C.
$[\alpha]_D{}^{35}= -3.59°$ (c=1.07, CH$_2$Cl$_2$)

NMR (CDCl$_3$) δ: 0.85–2.93 (27H, m), 3.34–3.40 (1H, m), 3.97–4.27 (2H, m), 6.94–7.53 (8H, m)

Preparation 6

The starting phenol derivative (10.0 g) of the following formula:

n-C$_8$H$_{17}$O—⟨phenyl⟩—⟨phenyl⟩—OH and the same R—(—)—epichlorohydrin (18.6 g) as used in Preparation 3, piperidine (367 ml) and dimethylformamide (1 ml) are mixed and stirred at 60° C. for 10 hours. The reaction mixture is distilled under reduced pressure to remove the solvent, and thereto is added acetone (5 ml) and further added dropwise 24 wt. % aqueous sodium hydroxide (1.2 equivalent) with stirring at room temperature, and the mixture is reacted for 30 minutes. The reaction mixture is adjusted to pH 7 with 2N hydrochloric acid and extracted with ethyl acetate. The extract is dried over anhydrous magnesium sulfate and distilled under reduced pressure to remove the solvent. The residue is purified by silica gel chromatography to give S isomer of a glycidyl ether (1.58 g) of the following formula:

n-C$_8$H$_{17}$O—⟨phenyl⟩—⟨phenyl⟩—O—CH$_2$—⟨epoxide⟩ m.p. 131° C.
$[\alpha]_D^{27} = +3.03°$ (c=0.55, CH$_2$Cl$_2$)
NMR (CDCl$_3$) δ: 0.70–2.20 (17H, m), 2.55–3.00 (2H, m), 3.15–3.45 (1H, m), 3.75–4.20 (2H, m), 6.89 (2H, d, J=9.0 Hz), 6.92 (2H, d, J=8.4 Hz), 7.43 (4H, d, J=9.0 Hz)

Preparation 7

A mixture of the starting phenol derivative (10 g) of the following formula:

n-C$_8$H$_{17}$O—⟨pyrimidine⟩—⟨phenyl⟩—OH, the same R—(—)—epichlorohydrin (16.07 g) as used in Preparation 3, 20 wt. % aqueous sodium hydroxide (7.33 g) and dimethylformamide (20 ml) is heated with stirring at 60°–70° C. for one hour. The reaction mixture is cooled and thereto is added water. The mixture is extracted with dichloromethane to obtain a crude product (11.67 g). The crude product is purified by silica gel column chromatography to give S isomer of a glycidyl ether (9.07 g) of the following formula:

n-C$_8$H$_{17}$O—⟨pyrimidine⟩—⟨phenyl⟩—O—CH$_2$—⟨epoxide⟩ m.p. 74° C.

$[\alpha]_D^{24} = +1.66°$ (c=1.02, CH$_2$Cl$_2$)
NMR (CDCl$_3$) δ: 0.5–2.2 (15H, m), 2.6–3.0 (2H, m), 3.1–3.7 (1H, m), 3.8–4.4 (4H, m), 6.95 (2H, d, J=9.0 Hz), 8.26 (2H, d, J=9.0 Hz), 8.36 (2H, s)

Preparation 8

A mixture of the starting phenol derivative (7.44 g) of the following formula:

n-C$_8$H$_{17}$O—⟨phenyl⟩—⟨pyrazine⟩—⟨phenyl⟩—OH as prepared in Preparation 1, the same R—(—)—epichlorohydrin (9.16 g) as used in Preparation 3, 50 wt. % aqueous sodium hydroxide (1.74 g) and dimethylformamide (77 ml) is stirred at 60°–70° C. for 3 hours. The reaction mixture is cooled and thereto is added water, and the mixture is extracted with dichloromethane. The extracted product is purified by silica gel column chromatography to give S isomer of a glycidyl ether (6.90 g) of the following formula:

n-C$_8$H$_{17}$O—⟨phenyl⟩—⟨pyrazine⟩—⟨phenyl⟩—O—CH$_2$—⟨epoxide⟩ m.p. 198° C.
$[\alpha]_D^{25} = +0.95°$ (c=1.04, CH$_2$Cl$_2$)
NMR (CDCl$_3$) δ: 0.6–2.1 (15H, m), 2.6–3.0 (2H, m), 3.2–3.5 (1H, m), 3.8–4.5 (2H, m), 6.99 (4H, d, J=9.0 Hz), 7.50 (2H, J=9.0 Hz), 8.40 (2H, d, J=9.0 Hz), 8.90 (2H, s)

Preparation 9

The starting phenol derivative (1.01 g) of the following formula:

n-C$_8$H$_{17}$—⟨pyrimidine⟩—⟨phenyl⟩—OH, the same R—(—)—epichlorohydrin (2.01 g) as used in Preparation 3 and benzyltriethylammonium chloride (16 mg) are mixed and heated at 70° C., and thereto is added dropwise 24 wt. % aqueous sodium hydroxide (650 mg). The mixture is stirred at 70° C. for 2 hours. The reaction mixture is left to stand to be cooled to room temperature and extracted three times with chloroform. The extract is dried over anhydrous magnesium sulfate and distilled under reduced pressure to remove the solvent. The residue is recrystallized from hexane to give S isomer of a glycidyl ether (380 mg) of the following formula:

n-C$_8$H$_{17}$—⟨pyrimidine⟩—⟨phenyl⟩—O—CH$_2$—⟨epoxide⟩ m.p. 65° C.

$[\alpha]_D^{25} = +1.90°$ (c=0.46, CH$_2$Cl$_2$)

NMR (CDCl$_3$) δ: 0.6–3.0 (19H, m), 3.2–3.6 (1H, m), 3.9–4.5 (2H, m), 6.99 (2H, d, J=9.0 Hz), 8.36 (2H, d, J=9.0 Hz), 8.55 (2H, s)

Preparation 10

A mixture of the starting phenol derivative (3.12 g) of the following formula:

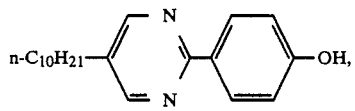

the same R—(−)—epichlorohydrin (4.627 g) as used in Preparation 3, 50 wt. % aqueous sodium hydroxide (0.88 g) and dimethylformamide (30 ml) is heated with stirring at 60° C. for 2.5 hours. The reaction mixture is cooled and distilled under reduced pressure to remove the solvent. The product is purified by silica gel column chromatography to give S isomer of a glycidyl ether (2.96 g) of the following formula:

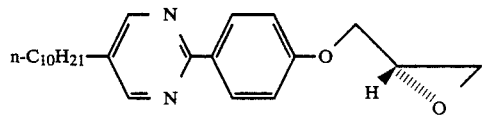

m.p. 65° C.
$[\alpha]_D^{27} = +2.47°$ (c=1.02, CH$_2$Cl$_2$)

NMR (CDCl$_3$) δ: 0.6–2.0 (19H, m), 2.4–3.0 (4H, m), 3.2–3.5 (H, m), 3.8–4.5 (2H, m), 6.98 (2H, d, J=9.0 Hz), 8.33 (2H, d, J=9.0 Hz), 8.53 (2H, s)

Preparation of Compound (A)

Preparation 11

To a solution of 4-(4-n-octylphenyl)-2-cyanophenol (1.9 g) prepared in Preparation 2 in t-butyl alcohol (40 ml) is added potassium t-butoxide (832 mg). After a short period of time, R—(−)—epichlorohydrin (2.5 ml) and 4-(N,N-dimethylamino)pyridine (100 mg) are added to the mixture, and the mixture is stirred at room temperature for 2 days. The reaction mixture is concentrated under reduced pressure, and to the residue is added water. The mixture is extracted with ether and the extract is dried and distilled to remove ether. The crude product thus obtained is purified by silica gel column chromatography to give S isomer of a glycidyl ether (750 mg) of the following formula:

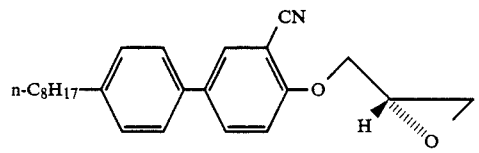

m.p. 54° C.
$[\alpha]_D^{23} = +7.88°$ (c=1.01, CH$_2$Cl$_2$)

NMR (CDCl$_3$) δ: 0.88 (3H, t, J=6.6 Hz), 1.20–1.42 (10H, m), 1.55–1.67 (2H, m), 2.64 (2H, t, J=7.7 Hz), 2.84–2.97 (2H, m), 3.39–3.43 (1H, m), 4.12–4.45 (2H, m), 7.05–7.77) (7H, m) IR (KBr): 2224 cm$^{-1}$ ($\gamma_{C\equiv N}$)

Preparation 12

The S isomer of glycidyl ether prepared in Preparation 3 (370 mg), diethyl n-propylmalonate (442 mg), potassium t-butoxide (134 mg) and t-butyl alcohol (3 ml) are mixed, and the mixture is refluxed with stirring for 10 hours. The reaction mixture is cooled to room temperature and thereto is added dropwise 4N hydrochloric acid until pH 1. The mixture is washed with water and methanol to give white crystals. The product is separated and purified by silica gel column chromatography to give γ-lactone derivatives, (2S, 4S) isomer (240 mg) and (2R, 4S) isomer (140 mg) of the following formulae:

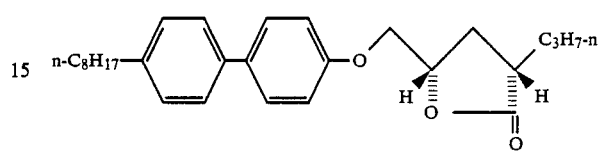

Phase transfer temperature:

$$C \xrightarrow[115° C.]{} I$$

$[\alpha]_D^{26} = +32.67°$ (c=1.081, CH$_2$Cl$_2$)

NMR (CDCl$_3$) δ: 0.70–3.00 (27H, m), 4.00–4.25 (2H, m), 4.40–4.85 (1H, m), 6.60–7.60 (8H, m)

IR (KBr): 1762 cm$^{-1}$ (2R, 4S) isomer:

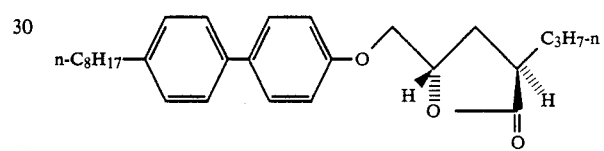

Phase transfer temperature:

$$C \xrightarrow[117° C.]{} I$$

$[\alpha]_D^{26} = +22.50°$ (c=0.504, CH$_2$Cl$_2$)

NMR (CDCl$_3$) δ: 0.70–3.00 (27H, m), 4.00–4.25 (2H, m), 4.50–5.00 (1H, m), 6.60–7.60 (8H, m)

IR (KBr): 1762 cm$^-$

Preparation 13

The S isomer of glycidyl ether prepared in Preparation 4 (365 mg), dimethyl malonate (232 mg), potassium t-butoxide (138 mg) and t-butyl alcohol (2 ml) are mixed, and the mixture is refluxed with stirring for 2 hours. The reaction mixture is cooled to room temperature and thereto is added dropwise 4N hydrochloric acid until pH 1. The mixture is extracted three times with chloroform, and the extract is washed with a saturated saline solution, dried over anhydrous magnesium sulfate and distilled under reduced pressure to remove the solvent. The residue is purified by silica gel column chromatography to give 4S isomer of a 2-(methoxycarbonyl)-γ-lactone derivative (226 mg) of the following formula:

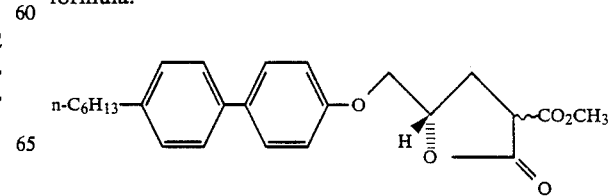

IR (KBr): 1740, 1768 cm$^{-1}$

The above γ-lactone derivative (200 mg), magnesium chloride (232 mg), dimethylacetamide (1.5 ml) and water (0.5 ml) are mixed and the mixture is refluxed with stirring for 10 hours. The reaction mixture is cooled to room temperature and extracted twice with chloroform. The extract is washed with a saturated saline solution, dried over anhydrous magnesium sulfate and distilled under reduced pressure to remove the solvent. The residue is purified by silica gel column chromatography to give 4S isomer of a γ-lactone derivative (145 mg) of the following formula:

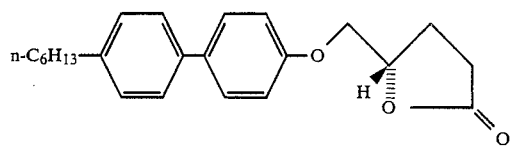

Phase transfer temperature:

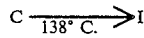

$[\alpha]_D^{30} = +19.16°$ (c=1.03, CH$_2$Cl$_2$)
NMR (CDCl$_3$) δ: 0.80–1.75 (11H, m), 2.15–2.85 (6H, m), 4.05–4.30 (2H, m), 4.75–4.95 (1H, m), 6.85–7.60 (8H, m)
IR (KBr): 1764 cm$^{-1}$

Preparation 14

The procedures of Preparation 12 are repeated except that the R isomer of glycidyl ether as prepared in Preparation 5 is employed as the optically active glycidyl ether and dimethyl n-butylmalonate is employed in place of diethyl n-propylmalonate to give γ-lactone derivatives, (2R, 4R) isomer and (2S, 2R) isomer of the following formulae:

(2R, 4R) isomer:

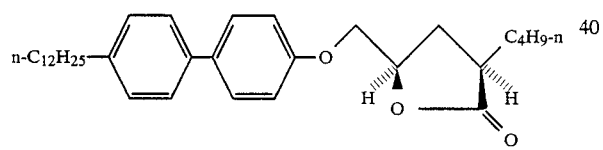

Phase transfer temperature:

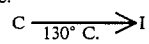

$[\alpha]_D^{34} = -28.56°$ (c=1.06, CH$_2$Cl$_2$)
NMR (CDCl$_3$) δ: 0.85–2.69 (37H, m), 4.15–4.18 (2H, m), 4.71–4.77 (1H, m), 6.95–7.53 (8H, m)
IR (KBr): 1764 cm$^{-1}$
(2S, 4R) isomer:

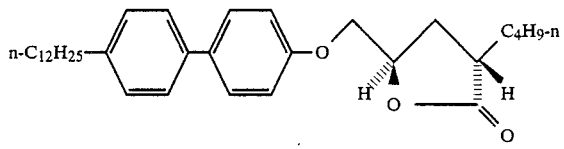

Phase transfer temperature:

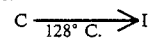

$[\alpha]_D^{34} = -22.98°$ (c=1.07, CH$_2$Cl$_2$)
NMR (CDCl$_3$) δ: 0.85–2.85 (37H, m), 4.08–4.21 (2H, m), 4.81–4.86 (1H, m), 6.93–7.52 (8H, m)
IR (KBr): 1760 cm$^{-1}$

Preparation 15

The S isomer of glycidyl ether prepared in Preparation 6 (260 mg), dimethyl n-octylmalonate (269 mg), potassium t-butoxide (90 mg) and t-butyl alcohol (2 ml) are mixed, and the mixture is refluxed with stirring for 13 hours. After the reaction, the reaction mixture is treated in the same manner as described in Preparation 12 to give white crystals. The product is separated and purified by silica gel column chromatography to give a γ-lactone derivative, (2S, 4S) isomer (43 mg) of the following formula:

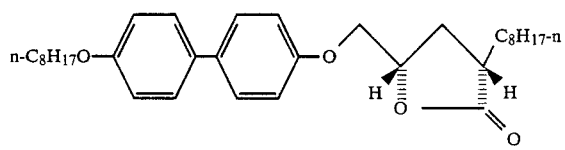

Phase transfer temperature:

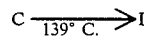

$[\alpha]_D^{30} = +28.59°$ (c=0.674, CH$_2$Cl$_2$)
NMR (CDCl$_3$) δ: 0.70–2.95 (37H, m), 3.80–4.20 (4H, m), 4.45–4.90 (1H, m), 6.90 (4H, d, J=9.0 Hz), 7.42 (4H, d, J=9.0 Hz)
IR (KBr): 1760 cm$^{-1}$

Preparation 16

The S isomer of glycidyl ether prepared in Preparation 8 (518 mg), dimethyl p-pentylmalonate (970 mg) and potassium t-butoxide (269 mg) are dissolved in dimethylformamide (5 ml) and t-butyl alcohol (5 ml) and the mixture is heated with stirring at 90° C. for 5 hours. After the reaction, the reaction mixture is treated in the same manner as described in Preparation 12 to give a γ-lactone derivative of the following formula. The obtained compound is a mixture of diastereomers, from which the (2R, 4S) isomer is separated by silica gel column chromatography.
(2R, 4S) isomer:

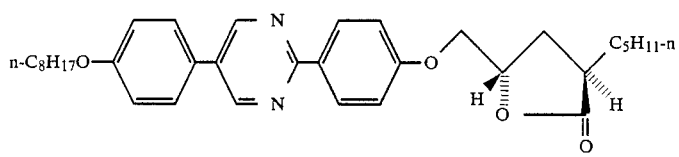

NMR (CDCl$_3$) δ: 0.4–3.0 (29H, m), 3.7–4.3 (4H, m), 4.82 (1H, m), 7.00 (4H, d, J=9.0 Hz), 7.50 (2H, d, J=9.0 Hz), 8.39 (2H, d, J=9.0 Hz), 8.85 (2H, s)

IR (nujol): 1778 cm$^{-1}$

Preparation 17

The S isomer of glycidyl ether prepared in Preparation 9 (320 mg), dimethyl n-hexylmalonate (406 mg) and potassium t-butoxide (116 mg) are dissolved in t-butyl alcohol (3.5 ml), and the mixture is refluxed with stirring for 6 hours. After the reaction, the reaction mixture is treated in the same manner as described in Preparation 12 to give a mixture of diastereomers of a γ-lactone derivative (270 mg, (2S, 4S)/(2R, 4S)=9/1).

(2S, 4S) isomer:

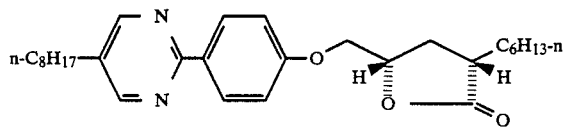

(2R, 4S) isomer:

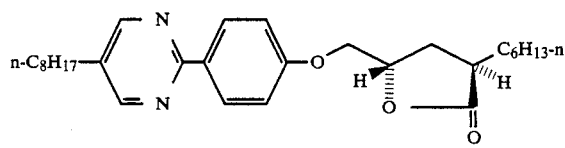

Physical properties of the mixture:

Phase transfer temperature:

$$C \xrightarrow{116° C.} I$$

$[α]_D^{25} = +37.93°$ (c=1.024, CH$_2$Cl$_2$)

NMR (CDCl$_3$) δ: 0.50–2.80 (33H, m), 4.10–4.25 (2H, m), 4.45–4.85 (1H, m), 6.95 (2H, d, J=9.0 Hz), 8.34 (2H, d, J=9.0 Hz), 8.52 (2H, s)

IR (nujol): 1778 cm$^{-1}$

Preparation 18

In the same manner as described in Preparation 17 except that the S isomer of glycidyl ether prepared in Preparation 10 is used as the optically active glycidyl ether and dimethyl n-dodecylmalonate is used in place of dimethyl n-butylmalonate, there are prepared γ-lactone derivatives, (2S, 4S) isomer and (2R, 4S) isomer.

(2S, 4S) isomer:

Phase transfer temperature:

$$C \xrightarrow{127° C.} I$$

$[α]_D^{31} = +26.01°$ (c=1.062, CH$_2$Cl$_2$)

NMR (CDCl$_3$) δ: 0.5–2.9 (49H, m), 4.19 (2H, m), 4.82 (1H, m), 6.95 (2H, d, J=9.0 Hz), 8.32 (2H, d, J=9.0 Hz), 8.52 (2H, s)

IR (nujol): 1778 cm$^{-1}$ (2R, 4S) isomer:

Phase transfer temperature:

$$C \xrightarrow{89° C.} I$$

$[α]_D^{31} = +17.12°$ (c=0.398, CH$_2$Cl$_2$)

NMR (CDCl$_3$) δ: 0.5–2.9 (49H, m), 4.19 (2H, m), 4.81 (1H, m), 6.95 (2H, d, J=9.0 Hz), 8.32 (2H, d, J=9.0 Hz), 8.52 (2H, s)

IR (nujol): 1778 cm$^{-1}$

Preparation 19

The S isomer of glycidyl ether prepared in Preparation 8 (518 mg), dimethyl n-undecylmalonate (1.37 g) and potassium t-butoxide (269 mg) are dissolved in dimethylformamide (5 ml) and t-butyl alcohol (5 ml) and the mixture is heated with stirring at 90° C. for 3 hours. After the reaction, the reaction mixture is treated in the same manner as described in Preparation 12 to give a γ-lactone derivative of the following formula (733 mg). The obtained compound is a mixture of diestereomers, from which the (2S, 4S) isomer and (2R, 4S) isomer are separated by silica gel column chromatography.

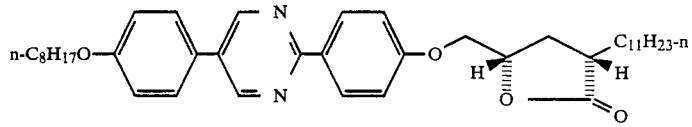

Phase transfer temperature:

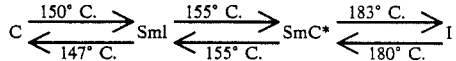

$[α]_D^{31} = +20.93°$ (c=1.116, CHCl$_3$)

NMR (CDCl$_3$) δ: 0.4–3.0 (41H, m), 3.7–4.3 (4H, m), 4.71 (1H, m), 7.00 (4H, d, J=9.0 Hz), 7.50 (2H, d, J=9.0 Hz), 8.39 (2H, d, J=9.0 Hz), 8.89 (2H, s)

IR (nujol): 1778 cm$^{-1}$ (2R, 4S) isomer

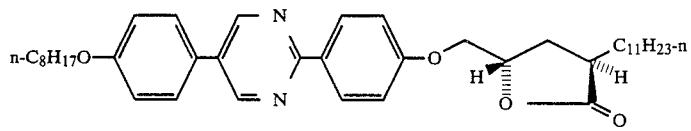

Phase transfer temperature:

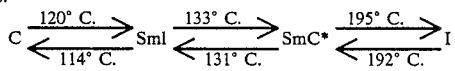

NMR (CDCl$_3$) δ: 0.4–3.0 (41H, m), 3.7–4.3 (4H, m), 4.83 (1H, m), 7.00 (4H, d, J=9.0 Hz), 7.50 (2H, d, J=9.0 Hz), 8.39 (2H, d, J=9.0 Hz), 8.89 (2H, s)

IR (nujol): 1778 cm$^{-1}$

Preparation 20

The S isomer of glycidyl ether prepared in Preparation 7 (1.00 g), dimethyl methylmalonate (677 mg) and potassium t-butoxide (630 mg) are dissolved in dimethylformamide (10 ml) and t-butyl alcohol (10 ml) and the mixture is heated with stirring at 90° C. for 2 hours. After the reaction, the reaction mixture is treated in the same manner as described in Preparation 12 to give a γ-lactone derivative of the following formula (810 mg). The obtained compound is a mixture of diastereomers, from which the (2S, 4S) isomer and (2R, 4S) isomer are separated by silica gel column chromatography.

(2S, 4S) isomer:

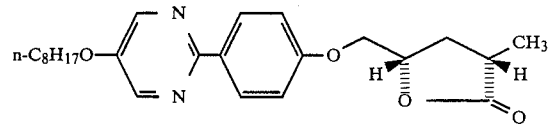

Phase transfer temperature:

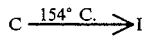

NMR (CDCl$_3$) δ: 0.5–3.0 (21H, m), 3.9–4.3 (4H, m), 4.65 (1H, m), 6.93 (2H, d, J=9.0 Hz), 8.25 (2H, d, J=9.0 Hz), 8.37 (2H, s)

IR (nujol): 1780 cm$^{-1}$ (2R, 4S) isomer:

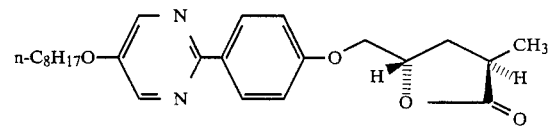

Phase transfer temperature:

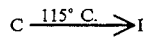

NMR (CDCl$_3$) δ: 0.5–3.0 (21H, m), 3.9–4.3 (4H, m), 4.75 (1H, m), 6.93 (2H, d, J=9.0 Hz), 8.25 (2H, d, J=9.0 Hz), 8.37 (2H, s)

IR (nujol): 1780 cm$^{-1}$

Preparation 21

A mixture of the S isomer of glycidyl ether (363 mg) obtained in Preparation 11, diethyl n-propylmalonate (303 mg), potassium t-butoxide (157 mg) and t-butyl alcohol (10 ml) is refluxed with stirring for 6 hours. The reaction mixture is cooled to room temperature and thereto is added water. The mixture is adjusted to pH 2 with 4N hydrochloric acid and is extracted with chloroform. The extract is distilled and the resulting oily substance is purified by silica gel column chromatography to give (2S, 4S) isomer (33 mg) and (2R, 4S) isomer (25 mg) of a γ-lactone of the following formulae.

(2S, 4S) isomer:

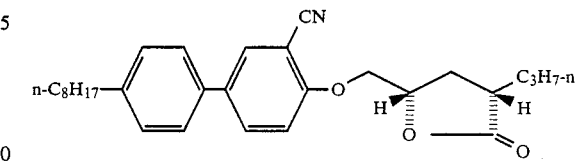

Phase transfer temperature:

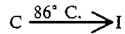

$[\alpha]_D^{23} = +31.83°$ (c=1.09, CH$_2$Cl$_2$)

NMR (CDCl$_3$) δ: 0.88 (3H, t, J=6.6 Hz), 0.97 (3H, t, J=7.1 Hz), 1.25–1.32 (10H, m), 1.41–1.58 (3H, m), 1.59–1.66 (2H, m), 1.85–2.07 (2H, m), 2.55–2.78 (4H, m), 4.31 (2H, d, J=4.3 Hz), 4.74–4.83 (1H, m), 7.00–7.77 (7H, m)

IR (KBr): 2232 cm$^{-1}$ ($\gamma_{C\equiv N}$), 1768 cm$^{-1}$ ($\gamma_{C=O}$)

(2R, 4S) isomer:

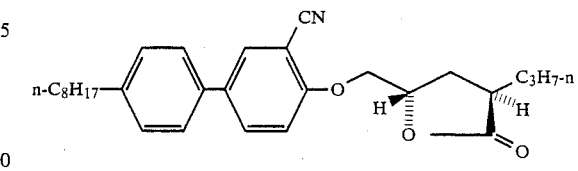

Phase transfer temperature:

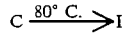

$[\alpha]_D^{23} = +18.26°$ (c=0.87, CH$_2$Cl$_2$)

NMR (CDCl$_3$) δ: 0.88 (3H, t, J=6.8 Hz), 0.98 (3H, t, J=7.1 Hz), 1.25–1.27 (12H, m), 1.45–1.56 (2H, m), 1.60–1.62 (1H, m), 1.85–1.95 (1H, m), 2.12–2.22 (1H, m), 2.56–2.67 (3H, m), 3.05–3.10 (1H, m), 4.19 (1H, dd, J=3.3, 10.3 Hz), 4.37 (1H, dd, J=3.3, 10.3 Hz), 4.84–4.89 (1H, m), 7.00–7.77 (7H, m)

IR (KBr): 2232 cm$^{-1}$ ($\gamma_{C\equiv N}$), 1768 cm$^{-1}$ ($\gamma_{C=O}$)

[Liquid crystal compositions containing the compound (A) and physical properties thereof]

EXAMPLE 1

The (2S, 4S) isomer of the γ-lactone derivative prepared in Preparation 12 of the following formula:

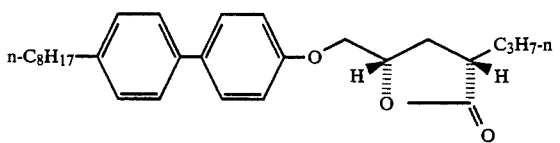

and a compound of the following formula (1):

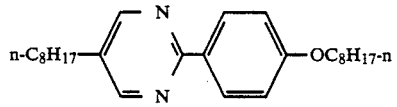

are mixed together at a weight ratio of 1:15.6 to give a liquid crystal composition.

The obtained liquid crystal composition is subjected to a DSC measurement, an observation with a polarization microscope and a measurement of the relative dielectric constant by a bridge method wherein the liquid crystal composition is sealed in a cell made of glass (thickness of spacer: 22 μm) and the cell is charged with alternating current (70 Hz, 1 V). As a result, the composition is proved to have the following phase transfer temperature:

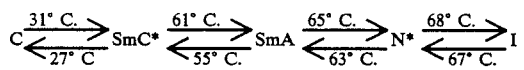

FIG. 1 shows the result of the measurement for the relative dielectric constant of the composition.

It is proved that the above (2S, 4S) isomer of the γ-lactone derivative alone does not show the ferro-electricity but it shows the ferroelectricity when it is mixed with other liquid crystalline compound.

EXAMPLE 2

The (2R, 4S) isomer of the γ-lactone derivative prepared in Preparation 12 of the following formula:

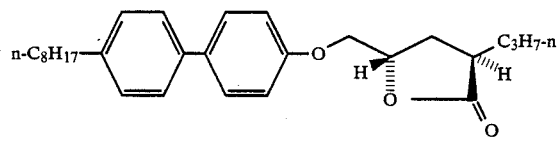

the compound (1) used in Example 1 are mixed together at a weight ratio of 1:18.0 to give a liquid crystal composition.

The phase transfer temperature of the obtained composition is measured in the same manner as described in Example 1. As a result, the composition shows the following phase transfer temperature:

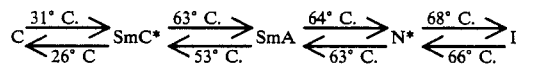

Figure 2:
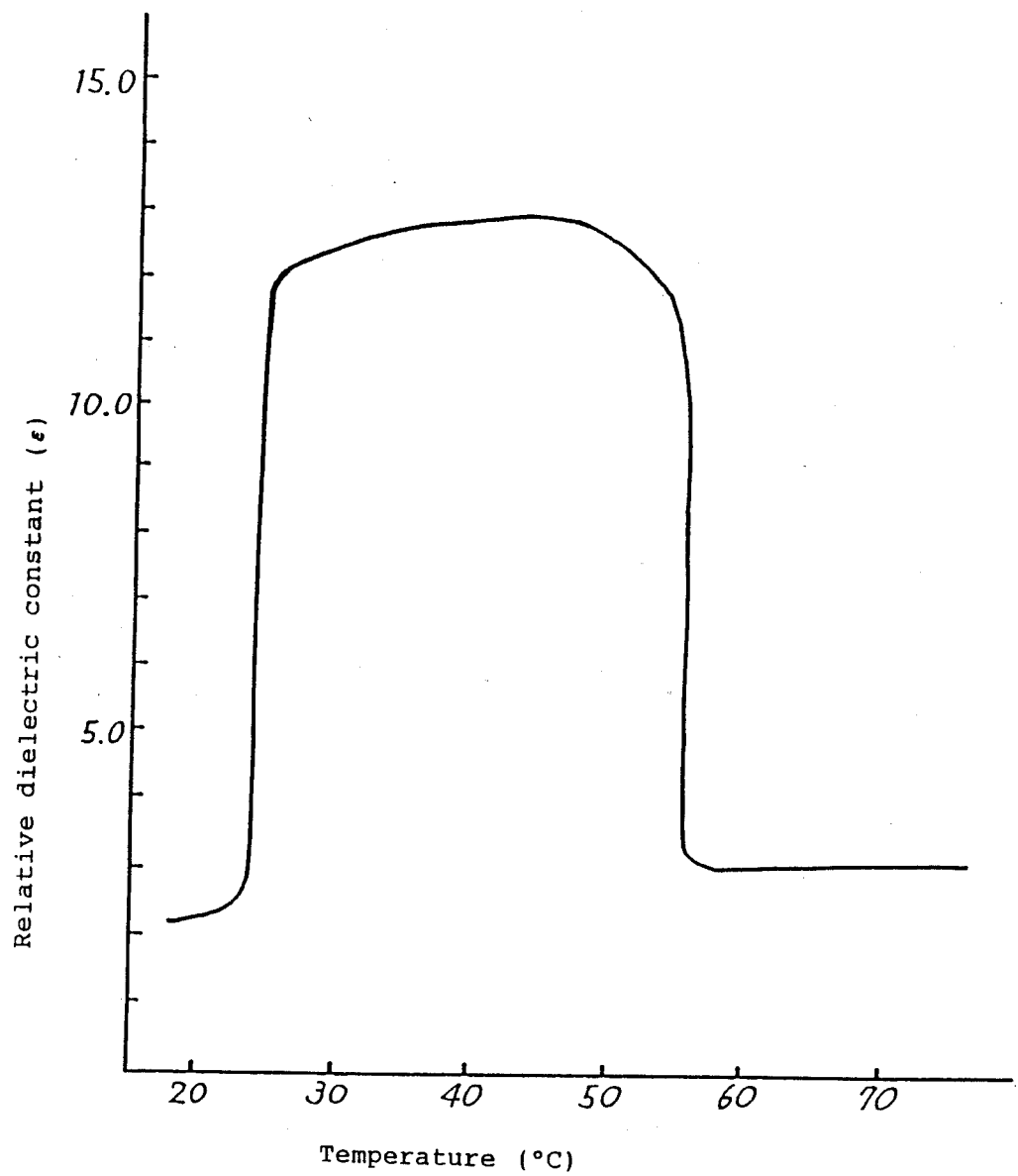
FIG. 2 shows a graph of the relation between the relative dielectric constant and temperature in the liquid crystal composition prepared in Example 2.

FIG. 2 shows the result of the measurement for the relative dielectric constant of the composition.

It is proved that the above (2R, 4S) isomer of the γ-lactone derivative alone does not show the ferro-electricity but it shows the ferroelectricity when it is mixed with other liquid crystalline compound.

EXAMPLE 3

The (4S) isomer of the γ-lactone derivative prepared in Preparation 13 of the following formula:

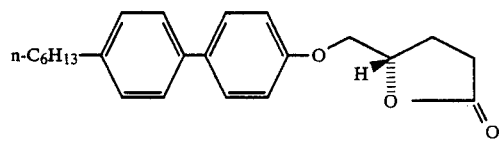

and a compound of the following formula (2):

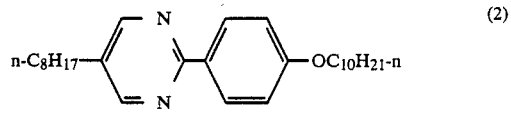

are mixed together at a weight ratio of 1:19 to give a liquid crystal composition.

The obtained liquid crystal composition is measured for the response speed. As a result, it is found that the composition shows the response speed as high as 490 μsec (40° C.). The response speed is measured in such a way that the above composition is sealed in a cell (thickness of spacer: 2 μm) surface-treated with an aligning agent and a change in strength of transmitted light is measured when the cell is charged with a voltage of $V_{p-p} = 20$ V with use of crossed nicols, wherein PET (polyethylene terephthalate) film as the spacer, polyimide film as the aligning agent and ITO (indium-tin oxide) electrode are employed and the rubbing is made in parallel direction.

EXAMPLE 4

The (2R, 4R) isomer of the γ-lactone derivative prepared in Preparation 14 of the following formula:

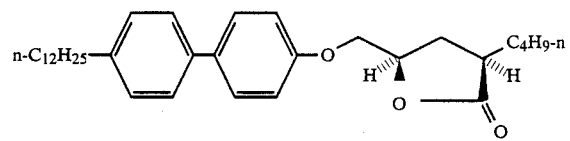

and the compound of the formula (2) used in Example 3 are mixed together at a weight ratio of 1:19 to give a liquid crystal composition.

The obtained composition is measured for the response speed in the same manner as described in Example 3. The result shows the response speed as high as 75 μsec (40° C.).

EXAMPLE 5

The (2S, 4S) isomer of the γ-lactone derivative prepared in Preparation 15 of the following formula:

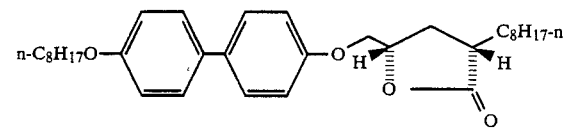

and the compound of the formula (1) used in Example 1 are mixed together at a weight ratio of 1:15.9 to prepare a liquid crystal composition. The phase transfer temperature of the obtained composition is measured in the same manner as described in Example 1. As a result, it is shown that the composition has the following phase transfer temperature:

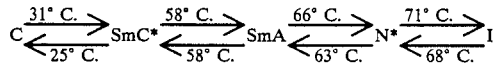

Figure 3:
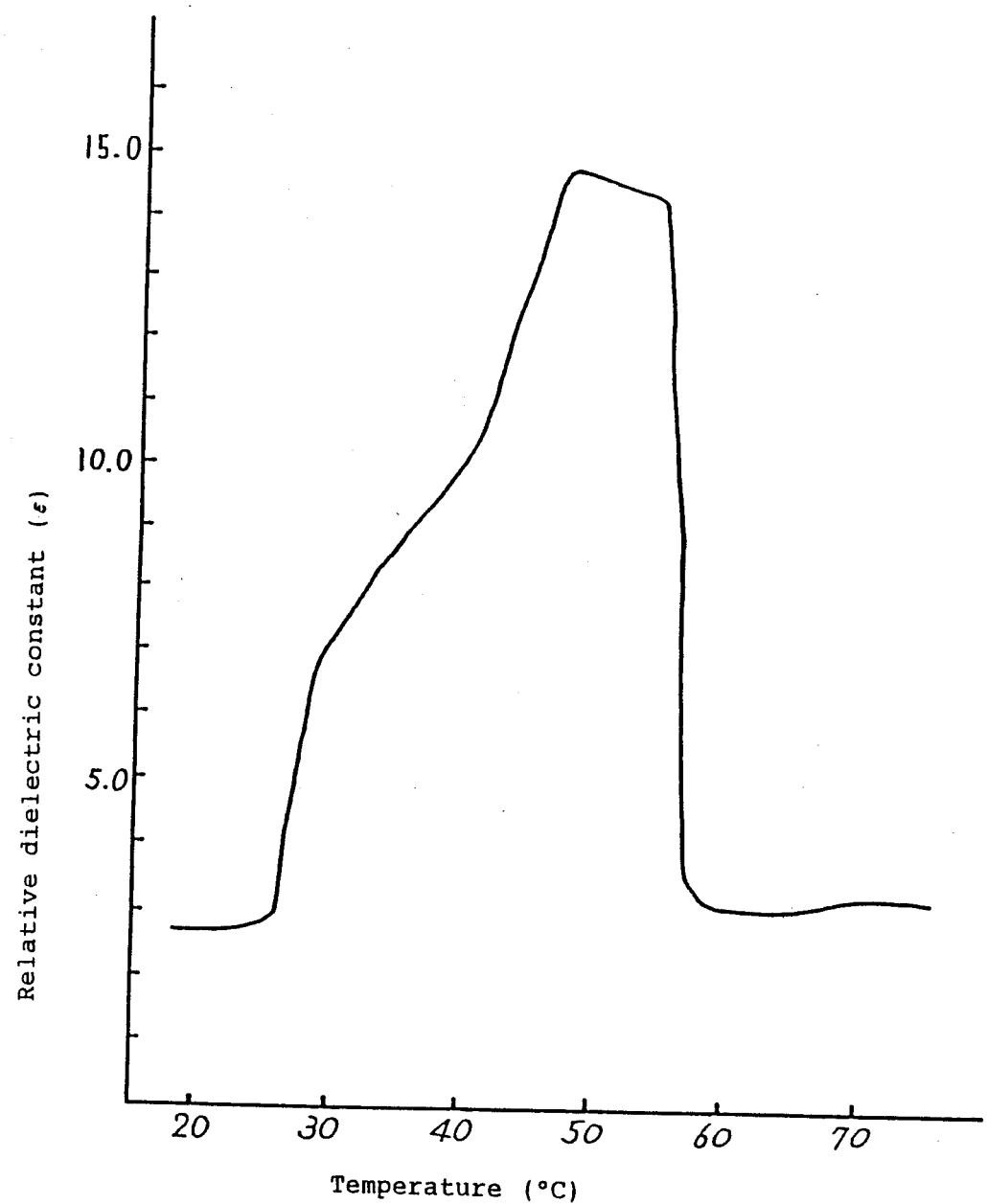
FIG. 3 shows a graph of the relation between the relative dielectric constant and temperature in the liquid crystal composition prepared in Example 5.

FIG. 3 shows the result of the measurement for the relative dielectric constant of the composition.

It is found that the above γ-lactone derivative alone does not show the ferroelectricity but it shows the ferroelectricity when it is mixed with other liquid crystalline compound.

EXAMPLE 6 AND COMPARATIVE EXAMPLE 1

The (2S, 4S) isomer of the γ-lactone derivative prepared in Preparation 15 of the following formula:

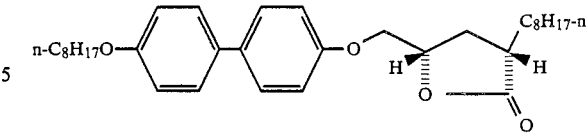

and the smectic liquid crystal components as shown in Table 1 are mixed together to prepare a liquid crystal composition.

The obtained liquid crystal composition is measured for the response speed in the same manner as described in Example 3. As a result, it is found that the liquid crystal composition comprising the γ-lactone derivative of this invention (Example 6) shows an extremely high response speed as compared to that of the liquid crystal composition without the γ-lactone derivative (Comparative Example 1).

TABLE 1

| Liquid crystalline compound | Ex. 6 | (wt %) Comp. Ex. 1 |
|---|---|---|
| n-C$_8$H$_{17}$O-⟨⟩-⟨⟩-O-CH$_2$-CH(H)-CH$_2$-CH(C$_8$H$_{17}$-n)-O-C(=O) (γ-lactone) | 10.0 | — |
| n-C$_8$H$_{17}$-⟨pyrimidine⟩-⟨⟩-OC$_{10}$H$_{21}$-n | 18.2 | 20.2 |
| n-C$_8$H$_{17}$O-⟨⟩-C(=O)-O-⟨⟩-OC$_5$H$_{11}$-n | 17.1 | 19.0 |
| n-C$_7$H$_{15}$O-⟨⟩-⟨⟩-C(=O)-O-⟨⟩-OC$_5$H$_{11}$-n | 14.8 | 16.4 |
| n-C$_8$H$_{17}$O-⟨⟩-O-C(=O)-⟨⟩-⟨⟩-O-CH$_2$(CH$_2$)$_4$-C*H(CH$_3$)-C$_2$H$_5$ | 20.6 | 23.0 |
| n-C$_8$H$_{17}$-⟨pyrimidine⟩-⟨⟩-O-CH$_2$(CH$_2$)$_4$-C*H(CH$_3$)-C$_2$H$_5$ | 19.3 | 21.4 |
| Response speed (μsec) | 50 (56° C.) | 1800 (50° C.) |

EXAMPLE 7

The (2R, 4S) isomer of the γ-lactone derivative prepared in Preparation 16 of the following formula:

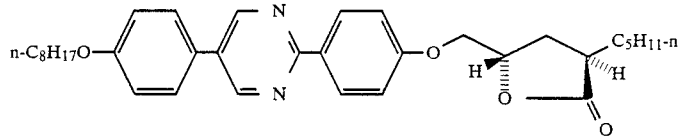

and the compound of the formula (1) used in Example 1 are mixed together at a weight ratio of 1:8.4 to prepare a liquid crystal composition.

The phase transfer temperature of the obtained composition is measured in the same manner as described in Example 1. As a result, it is shown that the composition has the following phase transfer temperature:

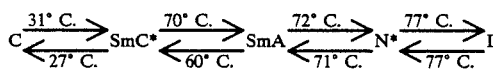

The above compound of the formula (1) has the following phase transfer temperature:

Therefore, by mixing the above (2R, 4S) isomer of the γ-lactone derivative with other liquid crystalline compound showing no ferroelectricity, the ferroelectricity is produced, and in addition, the obtained temperature range showing the ferroelectricity is much wider than that of the original SmC phase.

The same measurement is conducted on the (2S, 4S) isomer of the γ-lactone derivative which is separated concurrently with the (2R, 4S) isomer of the γ-lactone derivative, and as a result, the similar effect is shown.

EXAMPLE 8

The diastereomer mixture of the γ-lactone derivative prepared in Preparation 17 ((2S, 4S)/(2R, 4S)=9/1) of the following formulae:

(2S, 4S) isomer:

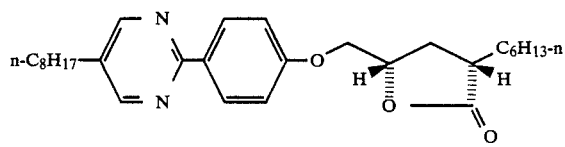

(2R, 4S) isomer:

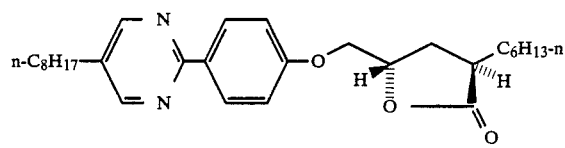

is mixed with the compound of the formula (1) used in Example 1 at a weight ratio of 1:9.7 to prepare a liquid crystal composition.

The phase transfer temperature of the obtained composition is measured in the same manner as described in Example 1. As a result, it is shown that the composition has the following phase transfer temperature:

Figure 4:
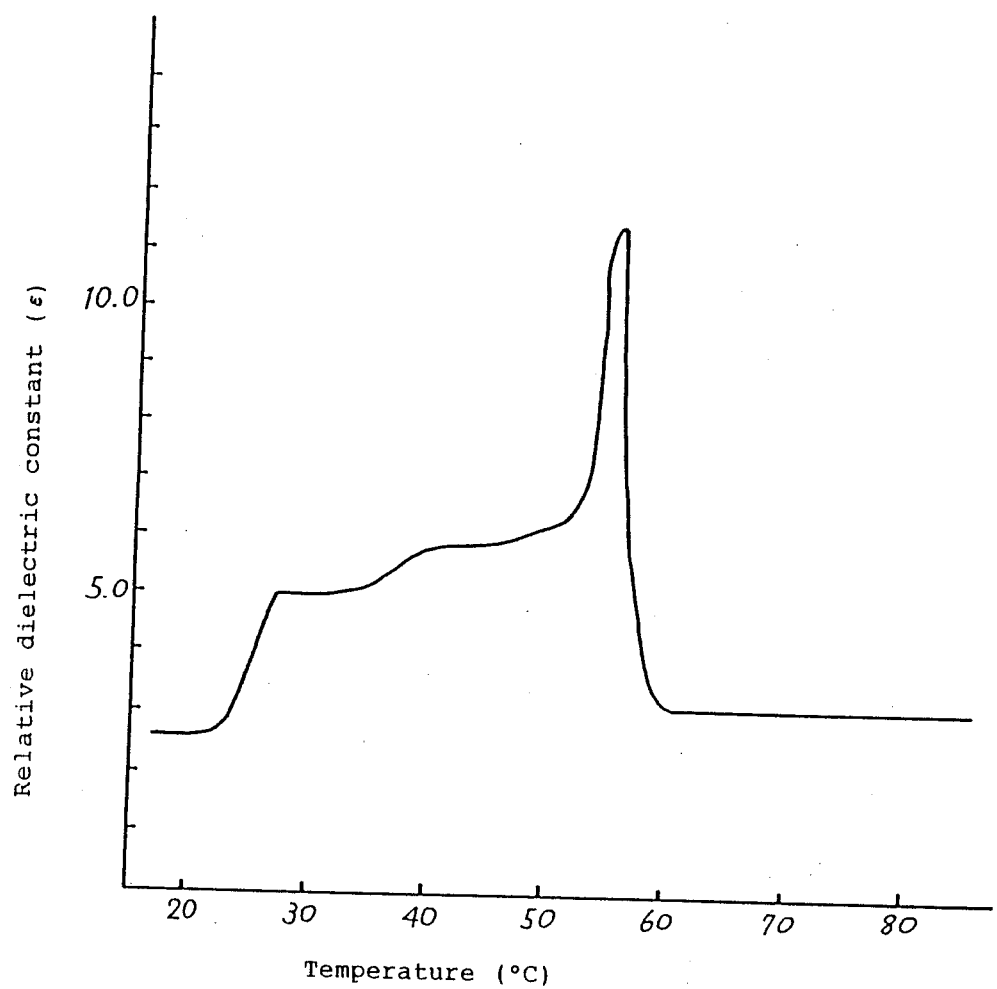
FIG. 4 shows a graph of the relation between the relative dielectric constant and temperature in the liquid crystal composition prepared in Example 8.

FIG. 4 shows the result of the measurement for the relative dielectric constant of the composition.

It is found that the above γ-lactone derivative alone does not show the ferroelectricity but it shows the ferroelectricity when it is mixed with other liquid crystalline compound.

EXAMPLE 9

The (2S, 4S) isomer of the γ-lactone derivative prepared in Preparation 18 of the following formula:

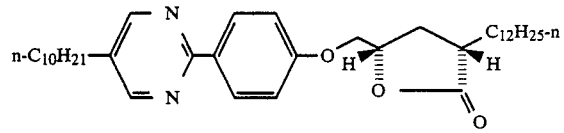

and the compound of the formula (2) used in Example 3 are mixed together at a weight ratio of 1:19 to prepare a liquid crystal composition.

The obtained composition is measured for the response speed in the same manner as described in Example 3, and as a result, it shows the response speed as high as 300 μsec (40° C.).

EXAMPLES 10 and 11

Using the (2S, 4S) isomer of the γ-lactone derivative prepared in Preparation 19 of the following formula:

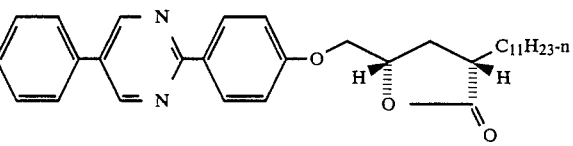

and the γ-lactone derivatives prepared in Preparation 20 as a mixture of (2S, 4S) isomer: (2R, 4S) isomer=1:1 of the following formulae:

(2S, 4S) isomer:

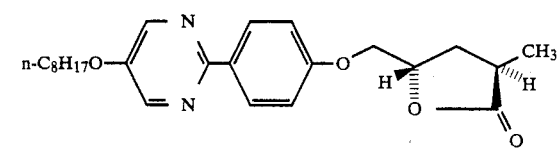

(2R, 4S) isomer:

liquid crystal compositions are prepared comprising the components as shown in Table 2.

The obtained compositions are measured on the phase transfer temperature and the response speed in the same manner as described in Example 3.

When the γ-lactone derivative of this invention is not contained in the liquid crystal composition, the response speed is as slow as 1800 μsec (50° C.) as shown in Comparative Example 1. On the contrary, the liquid crystal composition comprising the γ-lactone derivative of this invention shows much faster response speed, which proves that the liquid crystal composition of this invention is extremely useful for an element for display devices or an element for opto-electronics devices.

ity when it is mixed with other liquid crystalline compound.

The above composition is measured for the response speed in the same manner as described in Example 3, and as a result, it shows the response speed as high as 128 μsec (40° C.).

EXAMPLE 13

The (2R, 4S) isomer of the optically active γ-lactone

TABLE 2

| Liquid crystalline compound | Ex. 10 | (wt %) Ex. 11 |
|---|---|---|
| γ-Lactone deriv. (2S, 4S) isomer (Prep. 19) | 11.6 | — |
| γ-Lactone deriv. (2S, 4S) isomer (Prep. 20) | — | 4.9 |
| γ-Lactone deriv. (2R, 4S) isomer (Prep. 20) | — | 4.9 |
|  | 17.8 | 18.2 |
| 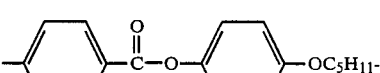 | 16.8 | 17.1 |
| 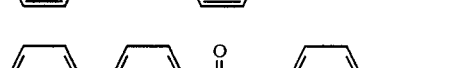 | 14.5 | 14.8 |
| 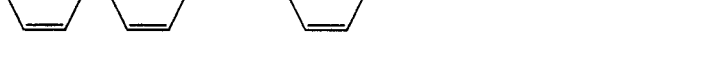 | 20.4 | 20.8 |
| 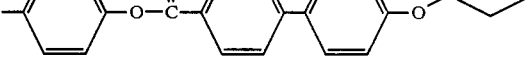 | 18.9 | 19.3 |
| Temperature range (SmC* phase)(°C.) | 35–68 | 28–68 |
| Response speed (μsec) | 150 (60° C.) | 140 (30° C.) |

EXAMPLE 12

The (2S, 4S) isomer of the optically active γ-lactone derivative prepared in Preparation 21 and a compound of the formula:

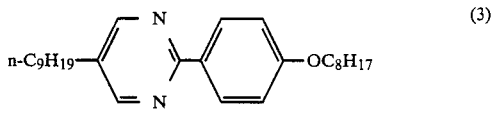 (3)

are mixed together at a weight ratio of 1:19 to prepare a liquid crystal composition.

By measuring in the same manner as described in Example 1, the liquid crystal composition thus obtained has the following phase transfer temperature:

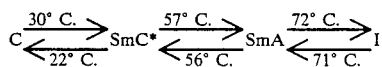

It is proved that the above (2S, 4S) isomer of the optically active γ-lactone derivative alone does not show the ferroelectricity but it shows the ferroelectricity when it is mixed with other liquid crystalline compound.

derivative prepared in Preparation 21 and the compound of the formula (3) used in Example 12 are mixed at a weight ratio of 1:19 to prepare a liquid crystal composition.

By measuring in the same manner as described in Example 1, the liquid crystal composition thus obtained has the following phase transfer termperature:

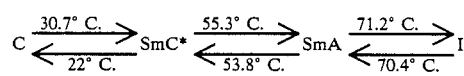

It is proved that the above (2R, 4S) isomer optically active γ-lactone derivative alone does not show the ferroelectricity but it shows the ferroelectricity when it is mixed with other liquid crystalline compound.

The above composition is measured for the response speed in the same manner as described in Example 3, and as a result, it shows the response speed as high as 98 μsec (40° C.).

What is claimed is:

1. A liquid crystal composition which comprises:

at least one liquid crystalline compound having an optically active γ-lactone ring of the formula (A):

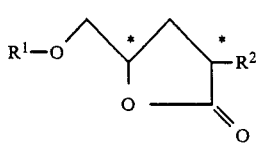 (A)

wherein $R^1$ is a member selected from the group consisting of

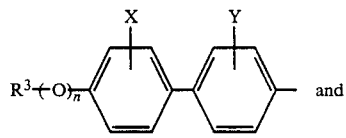 and

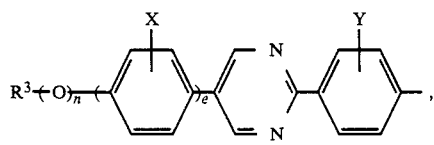, wherein n and e are each independently 0 or 1, $R^3$ is an alkyl group having 1 to 15 carbon atoms, X and Y are each independently a member selected from the group consisting of a hydrogen atom, a halogen atom and a cyano group;

$R^2$ has the formula $-(CO)_m-R^4$, wherein m is 0 or 1 and $R^4$ is a hydrogen atom or an alkyl group having 1 to 15 carbon atoms; and the symbol * is an asymmetric carbon atom; and a chiral or non-chiral liquid crystal compound selected from the group consisting of a compound of the formula (J-1):

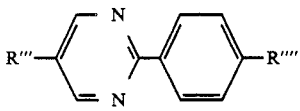 (J-1)

wherein $R'''$ and $R''''$ are the same or different and are each a straight chain or branched chain alkyl group having 1 to 15 carbon atoms or a straight chain or branched chain alkoxy group having 1 to 15 carbon atoms, said alkyl and alkoxy groups optionally having one or more asymmetric carbon atoms, and a compound of the formula (J-2):

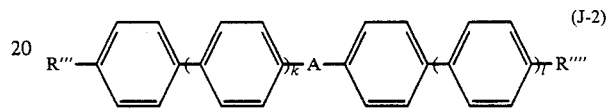 (J-2)

wherein $R'''$, and $R''''$ are as defined above, A is

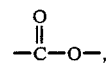

and k and l are independently 0 or 1, but $k+l \neq 2$.

2. The composition according to claim 1, wherein the compound of the formula (A) is in the form of a racemic mixture.

3. In an element for opto-electronic devices, the improvement which comprises a liquid crystal composition as set forth in claim 1.

4. In an element for opto-electronic devices, the improvement which comprises a liquid crystal composition as set forth in claim 2.

* * * * *